(12) United States Patent
Weber et al.

(10) Patent No.: US 7,375,111 B2
(45) Date of Patent: May 20, 2008

(54) COMPOSITIONS FOR AFFECTING WEIGHT LOSS

(75) Inventors: Eckard Weber, San Diego, CA (US); Michael Alexander Cowley, Portland, OR (US)

(73) Assignee: Orexigen Therapeutics, Inc., San Diego, CA (US)

( * ) Notice: Subject to any disclaimer, the term of this patent is extended or adjusted under 35 U.S.C. 154(b) by 339 days.

(21) Appl. No.: 10/828,795

(22) Filed: Apr. 21, 2004

(65) Prior Publication Data

US 2004/0254208 A1 Dec. 16, 2004

Related U.S. Application Data

(60) Provisional application No. 60/466,838, filed on Apr. 29, 2003.

(51) Int. Cl.
A61K 31/485 (2006.01)
A61K 31/137 (2006.01)

(52) U.S. Cl. .................. 514/282; 514/649; 514/321

(58) Field of Classification Search .................. None
See application file for complete search history.

(56) References Cited

U.S. PATENT DOCUMENTS

| | | | |
|---|---|---|---|
| 3,819,706 A | 6/1974 | Mehta | |
| 3,885,046 A | 5/1975 | Mehta | |
| 4,089,855 A | 5/1978 | Chatterjie et al. | |
| 4,172,896 A | 10/1979 | Uno et al. | |
| 4,513,006 A | 4/1985 | Maryanoff et al. | |
| 4,673,679 A | 6/1987 | Aungst et al. | |
| 4,689,332 A | 8/1987 | McLaughlin et al. | |
| 4,855,306 A | 8/1989 | Markstein et al. | |
| 5,312,925 A | 5/1994 | Allen et al. | |
| 5,358,970 A | 10/1994 | Ruff et al. | |
| 5,403,595 A * | 4/1995 | Kitchell et al. | 424/501 |
| 5,426,112 A | 6/1995 | Zagon et al. | |
| 5,427,798 A | 6/1995 | Ludwig et al. | |
| 5,486,362 A * | 1/1996 | Kitchell et al. | 424/426 |
| 5,512,593 A | 4/1996 | Dante | |
| 5,541,231 A | 7/1996 | Ruff et al. | |
| 5,719,197 A | 2/1998 | Kanios et al. | |
| 5,731,000 A | 3/1998 | Ruff et al. | |
| 5,763,493 A | 6/1998 | Ruff et al. | |
| 5,817,665 A | 10/1998 | Dante | 514/282 |
| 5,856,332 A | 1/1999 | Dante | |
| 5,958,962 A | 9/1999 | Cook | |
| 6,004,970 A | 12/1999 | O'Malley et al. | |
| 6,034,091 A | 3/2000 | Dante | |
| 6,048,322 A | 4/2000 | Kushida | |
| 6,071,537 A | 6/2000 | Shank | |
| 6,071,918 A * | 6/2000 | Cook | 514/321 |
| 6,110,973 A | 8/2000 | Young | |
| 6,150,366 A | 11/2000 | Arenson et al. | |
| 6,191,117 B1 | 2/2001 | Kozachuk | |
| 6,197,827 B1 * | 3/2001 | Cary | 514/646 |
| 6,210,716 B1 * | 4/2001 | Chen et al. | 424/497 |
| 6,245,766 B1 | 6/2001 | Watsky | |
| 6,248,363 B1 | 6/2001 | Patel et al. | |
| 6,262,049 B1 | 7/2001 | Coffin et al. | |
| 6,274,579 B1 | 8/2001 | Morgan et al. | |
| 6,323,236 B2 | 11/2001 | McElroy | |
| 6,344,474 B1 | 2/2002 | Maruani et al. | |
| 6,369,113 B2 * | 4/2002 | Young | 514/649 |
| 6,387,956 B1 | 5/2002 | Shapira | |
| 6,437,147 B1 | 8/2002 | Anderson et al. | |
| 6,441,038 B1 | 8/2002 | Loder et al. | |
| 6,481,031 B1 | 11/2002 | Hwang | |
| 6,506,799 B1 | 1/2003 | Dasseux | |
| 6,541,478 B1 | 4/2003 | O'Malley et al. | |
| 6,548,551 B2 | 4/2003 | Hinz | |
| 6,569,449 B1 | 5/2003 | Stinchcomb et al. | |
| 6,589,553 B2 * | 7/2003 | Li et al. | 424/461 |
| 6,686,337 B2 | 2/2004 | Connor | |
| 6,713,488 B2 | 3/2004 | Sadee et al. | |
| 6,905,708 B2 | 6/2005 | Li et al. | |
| 7,109,198 B2 | 9/2006 | Gadde et al. | |
| 2001/0025038 A1 | 9/2001 | Coffin et al. | |

(Continued)

FOREIGN PATENT DOCUMENTS

EP 0 442 769 A2 8/1991

(Continued)

OTHER PUBLICATIONS

"Approval Letter" of Application No. NDA 20-711, Department of Health & Human Services, May 14, 1997.*
Zhang et al. "Positional cloning of the mouse obese gene and its humane homologue," Nature 372:425-432 (1994).
Devlin et al. *Int. J. Eating Disord.* 28:325-332 (2000).
Cone et al. "The arcuate nucleus as a conduit for diverse signals relevant to energy homeostasis,"*Int'l Journal of Obesity*, 25(5):S63-S67 (2001).
Saper et al. "The need to feed: Homeostatic and hedonic control of eating," *Neuron*, 36:199-211 (2002).

(Continued)

*Primary Examiner*—Brian Kwon
(74) *Attorney, Agent, or Firm*—Knobbe, Martens, Olson and Bear LLP

(57) ABSTRACT

Disclosed are compositions for affecting weight loss comprising a first compound and a second compound, where the first compound is an opioid antagonist and the second compound causes increased agonism of a melanocortin 3 receptor (MC3-R) or a melanocortin 4 receptor (MC4-R) compared to normal physiological conditions. Also disclosed are methods of affecting weight loss, increasing energy expenditure, increasing satiety in an individual, or suppressing the appetite of an individual, comprising identifying an individual in need thereof and treating that individual to antagonize opioid receptor activity and to enhance α-MSH activity.

8 Claims, No Drawings

U.S. PATENT DOCUMENTS

| | | | |
|---|---|---|---|
| 2002/0025972 | A1 | 2/2002 | Hintz |
| 2002/0037836 | A1 | 3/2002 | Henriksen |
| 2002/0090615 | A1 | 7/2002 | Rosen et al. |
| 2002/0198227 | A1 | 12/2002 | Bernstein |
| 2003/0055008 | A1 | 3/2003 | Marcotte |
| 2003/0055038 | A1 | 3/2003 | Howard |
| 2003/0130322 | A1 | 7/2003 | Howard |
| 2003/0144174 | A1 | 7/2003 | Brenna et al. |
| 2003/0144271 | A1* | 7/2003 | Shulman ............... 514/214.03 |
| 2004/0002462 | A1 | 1/2004 | Najarian |
| 2004/0029941 | A1 | 2/2004 | Jennings |
| 2004/0033965 | A1 | 2/2004 | Gadde et al. |
| 2004/0106576 | A1 | 6/2004 | Jerussi et al. |
| 2004/0122033 | A1 | 6/2004 | Nargund et al. |
| 2004/0158194 | A1 | 8/2004 | Wolff et al. |
| 2004/0198668 | A1 | 10/2004 | Gadde et al. |
| 2004/0242974 | A1* | 12/2004 | Glover ....................... 600/300 |
| 2004/0254208 | A1 | 12/2004 | Weber et al. |
| 2005/0004106 | A1 | 1/2005 | Romano |
| 2005/0026986 | A1 | 2/2005 | Maruani et al. |
| 2005/0137144 | A1 | 6/2005 | Gadde et al. |
| 2005/0143322 | A1 | 6/2005 | Gadde et al. |
| 2005/0154002 | A1 | 7/2005 | Crooks et al. |
| 2005/0181070 | A1 | 8/2005 | Gadde et al. |
| 2005/0215552 | A1 | 9/2005 | Gadde et al. |
| 2005/0277579 | A1 | 12/2005 | Krishnano et al. |
| 2006/0009514 | A1 | 1/2006 | Gadde et al. |
| 2006/0058293 | A1 | 3/2006 | Weber et al. |
| 2006/0079501 | A1 | 4/2006 | Gadde et al. |
| 2006/0100205 | A1 | 5/2006 | Weber et al. |
| 2006/0122127 | A1 | 6/2006 | Rao et al. |
| 2006/0142290 | A1 | 6/2006 | Weber et al. |
| 2006/0160750 | A1 | 7/2006 | Gadde et al. |
| 2007/0117827 | A1 | 5/2007 | Tollefson et al. |

FOREIGN PATENT DOCUMENTS

| | | |
|---|---|---|
| RU | 2214241 | 6/1996 |
| WO | WO 90/13294 | 11/1990 |
| WO | WO 94/20100 | 9/1994 |
| WO | WO 96/09047 | 3/1996 |
| WO | WO 99/37305 | 7/1999 |
| WO | WO 00/51546 | 9/2000 |
| WO | WO 00/76493 | 12/2000 |
| WO | WO 01/62257 | 8/2001 |
| WO | WO 03/013524 | 2/2003 |
| WO | WO 03/092682 | 11/2003 |
| WO | WO 03/097046 | 11/2003 |
| WO | WO 03/097046 A1 | 11/2003 |
| WO | WO 2004/009015 | 1/2004 |
| WO | WO 2004/024096 A2 | 3/2004 |
| WO | WO 2004/050020 | 6/2004 |
| WO | WO 2004/050020 A2 | 6/2004 |
| WO | WO 2004/096201 | 11/2004 |
| WO | WO 2004/100992 A2 | 11/2004 |
| WO | WO 2004/110368 | 12/2004 |
| WO | WO 2004/110375 | 12/2004 |
| WO | WO 2005/000217 | 1/2005 |
| WO | WO 2005/049043 | 6/2005 |
| WO | WO 2006/017504 | 2/2006 |

OTHER PUBLICATIONS

Korner et al. "The emerging science of body weight regulation and its impact on obesity treatment," *J. Clin. Invest.*, 111(5):565-570 (2003).
Portoghese, P.S. *J. Med. Chem.*, 35:1927 (1992).
Carroll, F.I. *J. Med. Chem.*, 46:10 (2003).
Glass et al. *Neuropeptides*, 33:350 (1999).
Schmidhammer et al. *A. Helv. Chim. Acta*, 77:999 (1994).
Hahn et al. *J. Pharm. Exper. Therapeutics*, 235:846-850 (1985).
Kolb et al. *A. Pharmaceutical Res.*, 6:266-271 (1985).
Pasternak et al. *J. of Med. Chem.*, 23:674-676 (1980).
Le Bourdonnec et al. *J. Med. Chem.*, 43:2489-2492 (2000).
Sayre et al. *J. Med. Chem.*, 27:1325 (1984).
Erez et al. *J. Med. Chem.*, 25:847-849 (1982).
Dechant et al. *Drugs*, 41:225-253 (1991).
Tamiz et al. *J. Am. Chem. Soc.*, 122:5393-5394 (2000).
Tamiz et al. *J. Med. Chem.*, 44:1615:1622 (2001).
Hussey et al. *J. Am. Chem. Soc.*, 125:3692-3693 (2003).
Portoghese et al. *Life Sci.*, 31:1283-1286 (1982).
Portoghese et al. *J. Med. Chem.*, 29:1855-1861 (1986).
Stepinski et al. *Internat. J. of Peptide & Protein Res.*, 38:588-592 (1991).
Parr et al. *J. Immunol.*, 169:856-864 (2002).
Klok et al. *Macromolecules*, 35:746-759 (2002).
Portoghese et al. *J. Med. Chem.*, 29:1650-1653 (1986).
Sashiwa et al. *Macromolecules*, 33:6913 (2000).
Ninan et al. *Tetrahedron.*, 48:6709:16 (1992).
Zeng et al. *Tetrahedron Lett.*, 29:5123 (1988).
*Remington's Pharmaceutical Sciences*. 18th Edition; Easton, PA: Mack Publishing Co. (1990).
Fingl et al. *The Pharmacological Basis of Theraputics*. Ch.1, pp. 1. (1975).
Spigset, et al. *Therapeutic Approaches to Bulimia Nervosa*, Expert Opinion on Therapeutic Patents, vol. 11, No. 3, 2001, pp. 463-477; XP002292382.
Islam, et al. *Naltrexone, Serotonin Receptor Subtype Antagonists, and Carbohydrate Intake in Rats*, Pharmacology Biochemistry and Behavior, vol. 48, No. 1, 1994, pp. 193-201; XP002292383.
Olszewski, et al. *Evidence of Interactions Between Melanocortin and Opioid Systems in Regulation of Feeding*, Neuroreort, vol. 12, No. 8, Jun. 13, 2001, pp. 1727-1730: XP009035026.
Zhu, et al. *Pharmacologic Treatment of Easting Disorders*, Canadian Journal of Psychiatry, vol. 47 No. 3, Apr. 3, 2002 pp. 227-234; XP009035028.
Werneke, et al. *Options for Pharmacological Management of Obesity in patients Treated with Atypical Antipsychotics*, International Clinical Psychopharmacology, vol. 17 No. 4, 2002, pp. 145-160; XP009035036.
Fuller et al., *Fluoxetine: A Serotonergic Appetite Suppressant Drug*, Drug Development Research, vol. 17, No. 1, 1989, pp. 1-15; XP009035038.
"A Novel Twist on Binge Eating Treatment" Primary Psychiatry; 6(10) 24-29 (1999).
Anderson, et al. Bupropion SR enhances weight loss Obesity R., vol. 10, N. 7, 2002, pp. 633-641, XP002351373.
Altman and Bland. "Standard Deviations and Standard Errors," BMJ; 2005:331:903.
Appolinario et al. "Pharmacological Approaches in the Treatment of Binge Eating Disorder." Current Drug Targets; 5:301-307 (2004).
Asconape. "Some Common Issues in the Use of Antiepileptic Drugs." Seminars in Neurology; 22(1):27-39 (2002).
Atkinson, Clinical Guidelines on the identification, Evaluation, and pharamacologic treatment of obesity in Adults, Online, Jul. 25, 2003, URL:http://www.endotext.org.obesity/obesity15b/obesity15b.htm.
Ayala, "Weight Loss Associated With the Administration of Zonisamide", AES Proceedings, Epilepsia 41(Suppl. 7) :99 (2000) -No. 2.041.
Ayala et al, "Weight Loss Associated With the Administration of Zonisamide", A Compendium of Posters and Platform Sessions for ZONEGRAN™ and DIASTAT®, Presented at the Annual Meeting 2000 of the American Epilepsy Society, Dec. 1-6, 2000, Los Angeles, California.
Beelen, et al. "Asymptomatic QTC prolongation associated with queitiapine fumarate overdose in a patient being treated with risperidone" Human & Experimental Toxicology 92001) 20, 215-219.
Calabrese, et al. Letters to the Editors, "Lamotrigine and Clozapine for Bipolar Disorder" American J. of Psychiatry, vol. 157 9, Sep. 2000, 1523.
Carlsen, et al. "Evidence for dissociation of insulin-and weight-reducing of metformin in non-diabetic male patients with coronary heart disease" Diabetes Research and Clinical Practice Amersterdam, vol. 39, No. 1, Jan. 1998, pp. 47-54.

Chen, et al. "Synergistic Effects of Cannabiniod inverse agonist AM251 and opiod antagonist namefene on food intake" Brian Res. vol. 999, Jan. 2004, pp. 22-230.

Chengappa, et al. "Changes in body Weight and Body mass index among psychiatric patients receiving lithium, valproate, or topiramate: an open-label, nonrandomized chart review" Clinical Therapeutics, 24 (10) 1576-1584.

Dembowski, et al. "Successful Antimanic Treatment and Mood Stabilization with Lamotrigine, Clozapine, and Valproate in a Bipolar Patient after Lithium-induced Cerebellar Deterioration" Letter Pharmacopsychiatry, 2003; 36 83-86.

Diagnostic and Statistical Manual of Mental Disorders. 4th Edition, Text Revision, p. 583-595 (2000).

Dursen, et al., Clozapine Plus Lamotrigine in Treatment-Resistant Schizophrenia, Arch Gen Psychiatry vol. 56, Oct. 1999, 950-951.

Dursun, et al. "Lamotrgine-Clozapine Combination in Refractory Schizophrenia: Three Cases" J. Neuropsychiatry Clin. Neuroscience, 14:1, Winter 2002, 86.

Dursun, et al. "Augmenting Antipsychotic treatment with Lamotrigine or topiramate in patients with treatment-resistant Schizophrenia: a naturalistic case-series outcome study" Journal of Psychopharmacology 15(4) 2001-297-301.

Dursun, et al., "Psychopharmacology for the Clinician Psychopharmacologie Pratiqu" Journal of Psychiatry Neuroscience, vol. 26 No. 2, 2001, 168.

Dursun, et al. "Accelerated Weight Loss After Treating Refractory Depression with Fluoxetine Puls Topiramate: Possible Mechanism of Action" Canadian Journal of Psychiatry, vol. 46, No. 3 Apr. 2001, pp. 287-288.

Faught et al. "Randomized Controlled Trial of Zonisamide for the Treatment of Refractory Partial-Onset Seizures." Neurology; 57(10):1774-1779 (2001).

Gadde, et al. , "Zonisamide for Weight Loss in Obese Adults—A Randomized Controlled Trial" JAMA 289 (14): 1820-1825 (2003.

Gadde, et al. "Bupropion for Weight Loss: An Investigation of Efficacy and Toleability in Overweight and Obese Women" Obesity Reseach 9 (9): 544:551 (2001).

Gadde et al, "Randomized Controlled Trial of Zonisamide for Treating Obesity", American Epilepsy Society, http://164.109.45.39/submission/aes/status/..\preview.full.asp?presid=2%2E258, Sep. 11, 2002.

Gadde et al, "Randomized Trial of Weight Loss Efficacy of Zonisamide", No. 304, 26(Suppl. 1), Aug. 2002, International Journal of Obesity and Related Metabolic Disorders, Journal of the International Association for the Study of Obesity, Ninth International Congress on Obesity, Sao Paolo, Brazil, Aug. 24-29, 2002.

Gadde et al, "Zonisamide in Obesity: A 16 Week Randomized Trial", No. NR473, New Research, American Psychiatric Association 2002 Annual Meeting, May 18-23, 2002, Philadelphia, Pennsylvania.

Gadde and Logue, "Bupropion Sustained Release in Obesity: A Randomized Double-Blind, Placebo Controlled Study", No. NR634, New Research Program & Abstracts, American Psychiatric Association, 1999 Annual Meeting, The Clinician, May 15-20, 1999, Washington, D.C.

Gadde et al. Inpharma; 1383(84):9 (2003).

Gatley, et al. European Journal of Pharmacolgy, 307:331-338 (1996).

Ginsberg and Sussman, "Effects of Mood Stabilizers on Weight", Primary Psychiatry 7(5):49-58 (2000).

Grady, "Quest for Weight-Loss Drug Takes an Unusual Turn", The New York Times—Health, www.nytimes.com, Mar. 15, 2003.

Gordon, et al. "Mood Stablization and Weight Loss with Topiramate" American Journal of Psychiatry, American Psychiatric Association, Washington D.C. vol. 156, No. 6, Jun. 1999, pp. 968-969.

Harrison's Principles of Internal Medicine. Eleventh Edition, McGraw-Hill Book Company, p. 1921-1930 (1987).

Jallon et al. Drug Safety; 24(13):969-978 (2004).

Kiptoo, et al. Enchancement of Transdermal delivery or 6-B-naltrexol via a codrug linked to hydroxyburpropion, Journal of Controlled Release 113 (2006) 137-145.

Kirkham et al. Psychopharmacology 153:267-270(2001).

Leppik et al. Epilepsy Research; 14:165-173 (1993).

Lessig, et al., "Topiramate for Reversing Atypical Antipsychotic Weight Gain" J. Am. Child Adolesc. Psychiatry 40; Dec. 12, 2001. p. 1364.

Levy, et al., "Topiramate Produced Weight Loss Following Olanzapine-Induced Weight Gain in Schizophrenia" J. Clin. Psychiatry 63; Nov. 11, 2002, 1045.

Matsuura, "Indication for Anterior Temporal Lobectomy in Patients with Temporal Lobe Epilepsy and Psychopathology", Epilepsia 41(Suppl. 9) :39-42 (2000.

McElroy et al. "Zonisamide in the Treatment of Binge-Eating Disorder:An Open-Label, Prospective Trial." J. Clin. Psychiatry;65(1):50-56 (2004).

McElroy et al. Inpharma; 1428:10 (2004).

McLaughlin, et al, Behavorial Pharmacology, 14:583:588 (2003).

Morris, III, "The Effect of Zonisamide Administration on Patient Weight", A Scientific Exhibit at the American Epilepsy Society Annual Meeting, Dec. 3, 2000, Los Angeles, California.

Navarro, et al. "Topiramate for Clozapine-Induced Seizures" Am. J. Psychiatry 158; Jun. 6, 2001, 968-969.

NDA20-789, Zonegran (zonisamide) Capsules 100 mg, FDA Approved Labeling Text, p. 1-24 (Mar. 27, 2000).

Pasternak et al. J. of Med. Chem., 23:674-676 (1980).

Pavuluri, et al., Topiramate Plus Risperidone for Controlling Weight Gain and Symptoms in Preschool Mania, Journal of Child and Adolescent Psychopharmacology vol. 12 No. 3, 2002. p. 271-273.

Potter, et al. "Sustained Weight Loss Associated with 12-month topiramate Therapy" Epilepsia, Raven Press Ltd. New York, vol. 38, No. Suppl 8, 1997, p. 97.

Rowland, et al. Psychopharmacology, 159:111-116(2001).

Sackellares et al. Epilepsia; 26(3):206-211 (1985).

Schmidt et al. Epilepsy Research; 15:67-73 (1993).

Shapiro et al. "Additive Benefits of Combination Therapy with Sibutramine and Rimonabant on Body Weight, Insulin Sensitivity and Lipoproteins in Diet-Induced Obese Mice," 2005 NAASO Annual Meeting, Poster 405-P.

Shapira et al. "Treatment of Binge-Eating Disorder with Topiramate: A Clinical Case Series." J. Clin. Psychiatry; 61(5):368-371 (2000).

Shelton, Richard C., "Classification of Antidepressants and their Clinical Implications" Primary Care Companion J. Clin. Psychiatry 2003-5 (Supp. 7) pp. 27-32.

Thearle, et al. "Obesity and Pharmacology Endocrinology and Metabolism Clinics of North American" W.B. Suanders Company, Philadelphia US vol. 32, No. 4, pp. 1005-1024. (2003).

Wadden et al. "Effects of Sibutramine Plus Orlistat in Obese Women Following 1 Year of Treatment by Sibutramine Alone: A Placebo-Controlled Trial," Obesity Research; 8(6):431 (2000).

Walker et al, "Chronic Toxicity of the Anticonvulsant Zonisamide in Beagle Dogs", Fundamental and Applied Toxicology 11:333-342 (1988).

Wang, et al., "Gabapentin augmentation therapy in bipolar depression" Bipolar Disorders 2002, 4; 296-301.

Welty et al, "Weight Loss Associated With Use of Zonisamide in European and US Clinical Trials", A Compendium of Posters and Platform Sessions for Zonegran®, Presented at the Annual Meeting 2001 of the American Epilepsy Society, Nov. 30-Dec. 5, 2001, Philadelphia, Pennsylvania.

Wilding. Current Drug Targets; 5:325-332 (2004).

Wilner, "Is Weight Loss With Zonisamide Gender-Specific?", Dr. Tran, 2002 Annual Meeting of the American Epilepsy Society, https://secure.neurohub.net/cgi-perl/get.cgi?pub=52318&ext=htm.

Olsen, et al., "Conjugate Addition Ligands of Opioid Antagonists. Methacrylate Esters and Ethers of 6Alpha- And 6Beta-Naltrexol", Journal of Medicinal Chemistry, American Chemical Society, vol. 33:2, 1990, 737-741.

Strombert, et al., "A comparison of the effects of 6-beta naltrexol and naltrexone on the consumption of ehanol or sucrose using a limited-access procedure in rats." Pharmacology, Biochemistry, and Behavior, vol. 72, 2002, 483-490.

Aronne, et al. "Weight Gain in the Treatment of Mood Disorders"; J Clin Psychiatry 2003;64 (supple 8).

Blanchard, et al., "Pancreatitis Treated with Didanosine and Tenofabir Disoproxil Fumarate" Clinical Infectious Diseases, 2003;37 pgs 57-62.

Carpenter, et al. "Mirtazapine Augmentation in the Treatment of Refractory Depression"; J Clin Psychiatry 60:Jan 1, 1999.

Cash, et al. "Attitudes about antidepressants: Influence of information about weight-related side effects"; Perceptual and Motor Skills, 2000, 90, 453-456.

Deshmukh, et al. "Managing weight gain as a side effect of antidepressant therapy"; Cleveland Clinic Journal or Medicine vol. 70, Jul. 7, 2003.

Fava, Maurizio. "Weight Gain and Antidepresants"; J Clin Psychiatry 2000;61 (suppl 11).

Hashiguti, et al. "Simultaneous determination of in vivo hydroxylation of tyrosine and tryptophan in rat striatum by microdialysis-HPLC: relationship between dopamine and serotonin biosynthesis"; Journal of Neural Transmission (1993) 93:213-223.

Kossard, et al. Defining Urticarial Dermatitis; Arch Dermatol/vol. 142, Jan. 2006.

Malhotra, et al., "Medical Management of Obesity Associated With Mental Disorders", Journal or Clinical Psychiatry 2002;63[suppl 4]:24-32.

Okada, et al. "Effects of zonisamide on extracellular levels of monoamine and its metabolite, and on Ca2+ dependent dopamine release" Epilepsy Research, 13 (1992) 113-119.

Okada, et al. "Effects of zonisamide on dopaminergic system"; Epilepsy Research 22 (1995) 198-205.

Berke, et al., "Medical Management of Obesity", American Academy of Family Physicians, Jul. 15, 2000;62(2):419-26 Abstract.

Fukagawa et al., "Monoaminergic anorectic agents", Nippon Yikurigaku Zasshi, Nov. 2001;118(5):303-8, 2001 Abstract.

Gehlert D.R., et al., "The Selective Norepinephrine Reuptake Inhibitor, LY368975, Reduces Food Consumption in Animal Models of Feeding", J. Pharmacology and Experimental Therapeutics Oct. 1998;287(1):122-7 Abatract.

Kanba et al., Progress in Neuro-Psychopharmacology and Biological Psychiatry, 18(4), 707-715 (1994).

Michelson, et al., "Atomexetine in the Treatment of Children and Adolescents with Attention Deficit/Hyperactivity Disorder: A Randomized, Placebo-Controlled, Dose-Response Study", Pediatrics Nov. 2001;108(5):E83 Abstract.

Tollefson, et al., Am J. Psychiatry, 154(5), 457-465 (1997).

Croft et al., "Effect on body weight of bupropion sustained-release in patients with major depresssion treated for 52 weeks," Clinical Therapeutics 24(4):662-672 (Apr. 2002).

McDougle, et al., "A double-blind, placebo-controlled study of risperidone addition in serotonin reuptake inhibitor-refractory obsessive-compulsive disorder," Archive of General Psychiatry, 57(8):794-801 Aug. 2000.

Nash et al., "Anxiety disorders," Medicine, 32(7):17-21, Jul. 1, 2004.

Stein, "Neurobiology of the obsessive-compulsive spectrum disorders," Biological Psychiatry 47(4):296-304 Feb. 15, 2000.

Stein, "Obsessive-compulsive disorder," Lancet 360(9330):397-405 Aug. 3, 2002.

Astrup et al., "Thermogenic Synergism Between Ephedrine and Caffine in Healthy Volunteers: A Double-Blind, Placebo-Controlled Study", Metabolism, Mar. 1991, 323-329, vol. 40 (3).

Erfuth, et al. "Bupropion as add-on strategy in difficult-to-treat bipolar depressive patients", Neuropsychobiology, vol. 45, No. Supplement 1, Mar. 2002, pp. 33-36.

Greenway et al., "Double-Blind, Randomized, Placebo-Controlled Clinical Trials with Non-prescription Medications for the Treatment of Obesity", Obesity Research, Jul. 1999, 370-78, vol. 7(4).

Greenway et al., "A Long-acting Leptin Analog does not Enhance Fat, Visceral Fat, or Weight Loss When Combined with Caffeine Ephedrine in Obese Subjects", International Journal of Obesity, 2002, S136.

Greist, et al., "Double-blind Parallel Comparison of Three Dosages of Sertraline and Placebo in Outpatients With Obsessive-compulsive Disorder", Arch Gen Psychiatry, Apr. 1995, 52: 289-295.

Jain, et al. "Bupropin SR vs. Placebo for Weight Loss in Obese Patients with Depressive Symptoms", Obesity Research, Oct. 2002, 1049-56, vol. 10.

Kushner, et al. "Obesity pharmacology: past, present, and future.", Current Opinion in Gastroenterology, Mar. 2002, pp. 213-220.

Malcolm et al., "A Controlled Trial of Naltrexone in Obese Humans", International Journal of Obesity, Jun. 1985, 347-353, vol. 9.

Mitchell et al., "High-Dose Naltrexone Therapy and Dietary Counseling for Obesity", Biological Psychiatry, 1987, 35-42, vol. 22.

Penn, et al., "Pharmacotherapy of obesity in the near term.", Current Opinion in Endocrinology and Diabetes 2003 United States, 2003, pp. 311-316.

Rénéric, J. P. et al., "Opioid Receptor Antagonists in Psychiatry", CNS Drugs, Nov. 1998, 10 (5): 365-377.

Weintraub et al., "Long-term Weight Control Study I (weeks 0 to 34) 'The Enhancement of Behavior Modification, Caloric Restriction, and Exercise by Fenfluramine Plus Phentermine versus Placebo'", Clinical Pharmacology & Therapeutics, 1992, 586-94, vol. 51(5).

* cited by examiner

COMPOSITIONS FOR AFFECTING WEIGHT LOSS

RELATED APPLICATIONS

The present application claims priority to the Provisional Application Ser. No. 60/466,838, filed on Apr. 29, 2003, by Weber et al., and entitled "COMPOSITIONS FOR AFFECTING WEIGHT LOSS," the entire disclosure of which is incorporated herein by reference in its entirety.

BACKGROUND OF THE INVENTION

1. Field of the Invention

The present invention is in the field of pharmaceutical compositions and methods for the treatment of obesity and for affecting weight loss in individuals.

2. Description of the Related Art

Obesity is a disorder characterized by the accumulation of excess fat in the body. Obesity has been recognized as one of the leading causes of disease and is emerging as a global problem. Increased instances of complications such as hypertension, non-insulin dependent diabetes mellitus, arteriosclerosis, dyslipidemia, certain forms of cancer, sleep apnea, and osteoarthritis have been related to increased instances of obesity in the general population.

Obesity has been defined in terms of body mass index (BMI). BMI is calculated as weight $(kg)/[height\ (m)]^2$. According to the guidelines of the U.S. Centers for Disease Control and Prevention (CDC), and the World Health Organization (WHO) (World Health Organization. Physical status: The use and interpretation of anthropometry. Geneva, Switzerland: World Health Organization 1995. *WHO Technical Report Series*), for adults over 20 years old, BMI falls into one of these categories: below 18.5 is considered underweight, 18.5-24.9 is considered normal, 25.0-29.9 is considered overweight, and 30.0 and above is considered obese.

Prior to 1994, obesity was generally considered a psychological problem. The discovery of the adipostatic hormone leptin in 1994 (Zhang et al., "Positional cloning of the mouse obese gene and its human homologue," Nature 1994; 372:425-432) brought forth the realization that, in certain cases, obesity may have a biochemical basis. A corollary to this realization was the idea that the treatment of obesity may be achieved by chemical approaches. Since then, a number of such chemical treatments have entered the market. The most famous of these attempts was the introduction of Fen-Phen, a combination of fenfluramine and phentermine. Unfortunately, it was discovered that fenfluramine caused heart-valve complications, which in some cases resulted in the death of the user. Fenfluramine has since been withdrawn from the market. There has been some limited success with other combination therapy approaches, particularly in the field of psychological eating disorders. One such example is Devlin, et al., Int. J. Eating Disord. 28:325-332, 2000, in which a combination of phentermine and fluoxetine showed some efficacy in the treatment of binge eating disorders. Of course, this disorder is an issue for only a small portion of the population.

In addition to those individuals who satisfy a strict definition of medical obesity, a significant portion of the adult population is overweight. These overweight individuals would also benefit from the availability of an effective weight-loss composition. Therefore, there is an unmet need in the art to provide pharmaceutical compositions that can affect weight loss without having other adverse side effects.

SUMMARY OF THE INVENTION

Disclosed are compositions for affecting weight loss comprising a first compound and a second compound, where the first compound is an opioid antagonist and the second compound causes increased agonism of a melanocortin 3 receptor (MC3-R) or a melanocortin 4 receptor (MC4-R) compared to normal physiological conditions.

Also disclosed are methods of affecting weight loss, increasing energy expenditure, increasing satiety in an individual, or suppressing the appetite of an individual, comprising identifying an individual in need thereof and treating that individual to antagonize opioid receptor activity and to enhance α-MSH activity.

DETAILED DESCRIPTION OF THE PREFERRED EMBODIMENTS

Arcuate nucleus neurons are known to be responsive to a wide array of hormones and nutrients, including leptin, insulin, gonadal steroids, and glucose. In addition to potential transport mechanisms, peripheral substances may access these neurons via arcuate cell bodies in and projections to the median eminence, a region considered to be a circumventricular organ, which lacks a blood-brain barrier. Cone et al., "The arcuate nucleus as a conduit for diverse signals relevant to energy homeostasis," Int'l Journal of Obesity (2001) 25, Suppl 5, S63-S67.

Administration of exogenous leptin activates a number of different neurons in hypothalamic and brainstem cell groups that bear leptin receptor. Leptin-responsive neurons in the arcuate nucleus include both those containing neuropeptide Y (NPY) and agouti-related peptide (AgRP) in the medial part of the nucleus and those containing both pro-opiomelanocortin (POMC) and its derivatives, including α-melanocyte stimulating hormone (α-MSH), as well as cocaine and amphetamine-related transcript (CART). Saper et al., "The need to feed: Homeostatic and hedonic control of eating," Neuron, 36:199-211 (2002).

The leptin-responsive POMC neurons in the arcuate nucleus are thought to cause anorexia and weigh reduction by means of the action of α-MSH on melanocortin 3 and/or 4 receptors (MC3-R, MC4-R). The highest MC3-R expression level is in the hypothalamus and limbic system, whereas MC4-R mRNA is expressed in virtually all major brain regions. Some of the metabolic effects resulting from stimulation of MC4-R are decreased food intake and an increase in energy expenditure through stimulation of thyrotropin-releasing hormone and activation of the sympathetic nervous system. Targeted deletion of the MC4-R gene produces obesity, hyperphagia, hyperinsulinemia, and reduced energy expenditure. Targeted deletion of MC3-R results in increased adiposity due to decreased energy expenditure. Korner et al., "The emerging science of body weight regulation and its impact on obesity treatment," J. Clin. Invest. 111(5):565-570 (2003). Thus, increased concentrations of α-MSH in the central nervous system (CNS) increase its action on MC3-R and/or MC4-R and result in a suppressed appetite.

POMC neurons also release β-endorphin when they release α-MSH. β-endorphin is an endogenous agonist of the 1-opioid receptors (MOP-R), found on the POMC neurons. Stimulation of MOP-R decreases the release of α-MSH. This is a biofeedback mechanism that under normal physiological conditions controls the concentration of α-MSH in the CNS. Thus, blocking MOP-R by opioid antagonists will break the feedback mechanism, which results in continued secretion of α-MSH and an increase in its concentration in the CNS.

A second population of neurons in the arcuate nucleus tonically inhibits the POMC neurons. These POMC-inhibiting neurons secrete NPY, the neurotransmitter γ-aminobutyric acid (GABA), and AgRP. NPY and GABA inhibit POMC neurons, via NPY Y1 receptors and GABA receptors, respectivley. Thus, within the arcuate nucleus NPY and GABA inhibit the release of α-MSH, and therefore are stimulators of feeding. It is known that leptin inhibits the release of GABA from NPY terminals synapsing onto POMC neurons, whereas ghrelin, an orexigenic peptide, stimulates the ghrelin receptors on NPY neurons and increase the secretion of NPY and GABA onto the POMC cells, which in turn inhibits the release of α-MSH.

AgRP stimulates food intake in the rat through antagonism of the interaction of α-MSH at MC4-R. Expression of the AgRP gene is suppressed by leptin.

Serotonin, also known as 5-hydroxytryptamine or 5-HT, activates the POMC neurons to secrete α-MSH. However, serotonin is taken up and removed from action by specific transporters so that a single serotonin molecule has short term effects. It is known that selective serotonin re-uptake inhibitors (SSRIs) prevent the uptake of serotonin and increase its concentrations in the CNS. Thus, SSRIs also increase the secretion of α-MSH and its concentrations in the CNS.

Therefore, increased secretion of α-MSH through various mechanisms, such as serotonin re-uptake inhibition, are among the strategies that the methods and pharmaceutical compositions of the present invention pursue in order to produce a biochemical anorexigenic effect.

The present invention provides a multi-faceted combination therapy approach to the problem of weight loss. It addresses not just single molecules, messengers, or receptors, but instead acts on multiple points in the feeding and satiety pathway. Aspects of the present invention are directed to increasing the concentrations of α-MSH in the CNS by stimulating the release of A-MSH, suppressing its metabolism, reducing the antagonism of its interaction at MC3/4-R, and suppressing any feedback mechanisms that slow or stop its release. Aspects of the present invention include pharmaceutical compositions whose components achieve one or more of these functions. The present inventors have discovered that a combination of two or more of the compounds disclosed herein results in a synergistic effect that affects weight loss more quickly and on a more permanent basis.

Thus, in a first aspect, the present invention is directed to a composition for the treatment of obesity or for affecting weight loss comprising a first compound and a second compound, where the first compound is an opioid antagonist and the second compound causes increased agonism of a melanocortin 3 receptor (MC3-R) or a melanocortin 4 receptor (MC4-R) compared to normal physiological conditions.

In certain embodiments, the second compound causes increased activity of the POMC neurons, leading to greater agonism at MC3-R and/or MC4-R.

In certain embodiments the opioid antagonist antagonizes a µ-opioid receptor (MOP-R) in a mammal. The mammal may be selected from the group consisting of mice, rats, rabbits, guinea pigs, dogs, cats, sheep, goats, cows, primates, such as monkeys, chimpanzees, and apes, and humans.

In some embodiments the opioid antagonist is selected from the group consisting of alvimopan, norbinaltorphimine, nalmefene, naloxone, naltrexone, methylnaltrexone, and nalorphine, and pharmaceutically acceptable salts or prodrugs thereof.

In other embodiments, the opioid antagonist is a partial opioid agonist. Compounds of this class have some agonist activity at opioid receptors. However, because they are weak agonists, they function as de-facto antagonists. Examples of partial opioid agonists include pentacozine, buprenorphine, nalorphine, propiram, and lofexidine.

The term "pharmaceutically acceptable salt" refers to a formulation of a compound that does not cause significant irritation to an organism to which it is administered and does not abrogate the biological activity and properties of the compound. Pharmaceutical salts can be obtained by reacting a compound of the invention with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutical salts can also be obtained by reacting a compound of the invention with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl) methylamine, and salts thereof with amino acids such as arginine, lysine, and the like.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug, or may demonstrate increased palatability or be easier to formulate. An example, without limitation, of a prodrug would be a compound of the present invention which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to provide the active moiety.

In certain embodiments, the second compound in the pharmaceutical compositions of the present invention triggers the release of α-melanocyte stimulating hormone (α-MSH). The second compound may increase the extracellular serotonin concentrations in the hypothalamus. In some embodiments, the second compound is selected from the group consisting of a selective serotonin reuptake inhibitor (SSRI), a serotonin 2C agonist, and a serotonin 1B agonist. In further embodiments, the second compound is selected, e.g., from the group consisting of fluoxetine, fluvoxamine, sertraline, paroxetine, citalopram, escitalopram, sibutramine, duloxetine, atomoxatine, and venlafaxine, and pharmaceutically acceptable salts or prodrugs thereof.

The terms "serotonin 1B receptor," "serotonin 2C receptor," "5-HT1b receptor," and "5-HT2c receptor" refer to receptors found more commonly in rodents. It is understood by those of skill in the art that other mammals have serotonin receptors on various neurons that are analogous in function and form to these receptors. Agonists or antagonists at these non-rodent, preferably human, serotonin receptors are within the scope of the present invention.

In certain embodiments, the second compound suppresses the expression of the AgRP gene or the production or release of agouti-related protein (AgRP). In some of these embodiments, the second compound suppresses the activity of neurons that express AgRP.

In other embodiments, the second compound suppresses the expression of the NPY gene or the production or release of neuropeptide Y (NPY). In some of these embodiments, the second compound suppresses the activity of neurons that express NPY. In further embodiments, the second compound is selected from the group consisting of NPY antagonists, ghrelin antagonists, and leptin. In certain other embodiments, the second compound agonizes NPY Y2 receptor.

Other embodiments of the present invention include those in which the second compound is selected from the group consisting of a γ-amino butyric acid (GABA) inhibitor, a GABA receptor antagonist, and a GABA channel antagonist. By "GABA inhibitor" it is meant a compound that reduces the production of GABA in the cells, reduces the release of GABA from the cells, or reduces the activity of GABA on its receptors, either by preventing the binding of GABA to GABA receptors or by minimizing the effect of such binding. The GABA inhibitor may be a 5-HT1b agonist or another agent that inhibits the activity of NPY/AgRP/GABA neurons. In addition, the GABA inhibitor may suppress the expression of the AgRP gene, or the GABA inhibitor may suppress the production or release of AgRP. It is, however, understood that a 5-HT1b agonist may inhibit the NPY/AgRP/GABA neuron (and therefore activate POMC neurons) without acting as an inhibitor of the GABA pathway.

In certain other embodiments the GABA inhibitor increases the expression of the POMC gene. In some of these embodiments, the GABA inhibitor increases the production or release of pro-opiomelanocortin (POMC) protein. In certain other of these embodiments, the GABA inhibitor increases the activity on POMC expressing neurons. In some embodiments, the GABA inhibitor is topiramate.

In other embodiments the second compound is a dopamine reuptake inhibitor. Phentermine is an example of a dopamine reuptake inhibitor. In certain other embodiments, the second compound is a norepinephrine reuptake inhibitor. Examples of norepinephrine reuptake inhibitors include bupropion, thionisoxetine, and reboxetine. Other embodiments include those in which the second compound is a dopamine agonist. Some dopamine agonists that are available on the market include cabergoline, amantadine, lisuride, pergolide, ropinirole, pramipexole, and bromocriptine. In further embodiments, the second compound is a norepinephrine releaser, for example diethylpropion, or a mixed dopamine/norepinephrine reuptake inhibitor, for example, atomoxatine.

In certain other embodiments, the second compound is a 5-HT1b agonist, such as sumatriptan, almotriptan, naratriptan, frovatriptan, rizatriptan, zomitriptan, and elitriptan.

In further embodiments, the second compound is an anticonvulsant. The anticonvulsant may be selected from the group consisting of zonisamide, topiramate, nembutal, lorazepam, clonazepam, clorazepate, tiagabine, gabapentin, fosphenyloin, phenyloin, carbamazepine, valproate, felbamate, levetiracetam, oxcarbazepine, lamotrigine, methsuximide, and ethosuxmide.

In some embodiments, the second compound is a cannabinoid receptor antagonist. Examples of this group of compounds include AM251 [N-(piperidin-1-yl)-1-(2,4-dichlorophenyl)-5-(4-iodophenyl)-4-methyl-1H-pyrazole-3-carboxamide], AM281 [N-(morpholin-1-yl)-1-(2,4-dichlorophenyl)-5-(4-iodophenyl)-4-methyl-1H-pyrazole-3-carboxamide], AM630 (6-iodo-2-methyl-1-[2-(4-morpholinyl)ethyl]-1H-indol-3-yl](4-methoxyphenyl)methanone), LY320135, and SR141716A (rimonabant), and pharmaceutically acceptable salts or prodrugs thereof. LY320135 and SR141716A have the following structures.

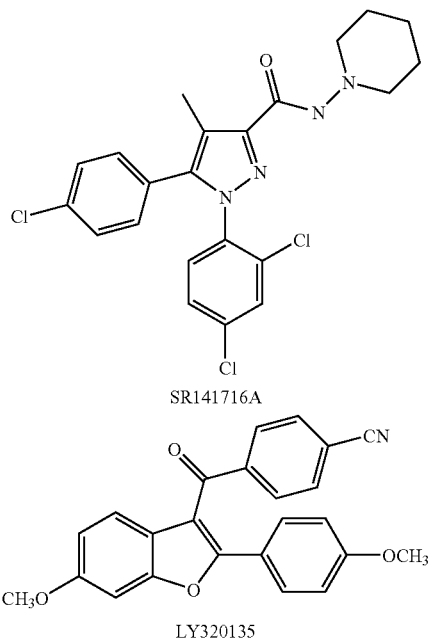

In certain embodiments, the second compound itself may be a combination of two or more compounds. For example, the second compound may be a combination of a dopamine reuptake inhibitor and a norepinephrine reuptake inhibitor, e.g. bupropion and mazindol. Alternatively, the second compound may be a combination of a SSRI and a norepinephrine reuptake inhibitor, such as sibutramine, venlafaxine, and duloxetine.

In certain embodiments, the second compound is an activator of the POMC neurons. Examples of POMC activators include Ptx1 and interleukin 1 beta, (IL-1β).

In another aspect, the present invention relates to a method of affecting weight loss, comprising identifying an individual in need thereof and treating that individual to antagonize opioid receptor activity and to enhance α-MSH activity.

In certain embodiments, the individual has a body mass index (BMI) greater than 25. In other embodiments, the individual has a BMI greater than 30. In still other embodiments, the individual has a BMI greater than 40. However, in some embodiments, the individual may have a BMI less than 25. In these embodiments, it may be beneficial for health or cosmetic purposes to affect weight loss, thereby reducing the BMI even further.

In some embodiments, opioid receptor activity is antagonized by administering an opioid receptor antagonist. The opioid receptor antagonist may be a MOP receptor antagonist. In some embodiments, the opioid receptor antagonist is selected from alvimopan, norbinaltorphimine, nalmefene, naloxone, naltrexone, methylnaltrexone, and nalorphine, and pharmaceutically acceptable salts or prodrugs thereof.

In some of the embodiments set forth above, α-MSH activity is enhanced by administering a compound, where the compound triggers release of α-MSH or increases the activity of neurons that express α-MSH. In some embodiments, the compound is a selective serotonin reuptake inhibitor (SSRI) or a specific 5-HT receptor agonist. Examples of SSRIs that can be used in the present invention include fluoxetine, fluvoxamine, sertraline, paroxetine, citalopram, escitalopram, sibutramine, duloxetine, and venlafaxine, and pharmaceutically acceptable salts or prodrugs thereof.

In other embodiments, the compound is a γ-amino butyric acid (GABA) inhibitor. The GABA inhibitor may be a 5-HT1b receptor agonist. The GABA inhibitor may suppress the expression of the AgRP gene, or it may suppresses the production or release of AgRP. The GABA inhibitor may suppress the expression or release of NPY. In certain embodiments, the GABA inhibitor suppresses the activity of neurons that express AgRP. For example, the GABA inhibitor may be topiramate, 1-(2-(((diphenylmethylene)amino) oxy)ethyl)-1,2,5,6-tetrahydro-3-pyridinecarboxylic acid hydrochloride (NNC-711), or vigabatrin.

In certain embodiments, the method of invention set forth above is practiced with the proviso that the individual is not suffering from Prader-Willi syndrome or binge eating disorder. Thus, some embodiments of the invention are to be distinguished from combination therapy involving SSRI anti-depressants (e.g., fluoxetine) used to treat physiological eating disorders such as binge eating disorder or Prader-Willi syndrome. In these embodiments, the target population is the population of individuals needing or desiring weight loss, apart from needing treatment for Prader-Willi syndrome or binge eating disorder.

Individuals suffering from depression may gain weight as a result of their depression. In addition, certain depressed individuals gain weight as a side effect of the depression therapy. In certain embodiments, the method of invention set forth above is practiced with the proviso that the individual is not suffering from depression. In some embodiments, the individual's overweight state was not caused by treatment for depression.

In other embodiments, the method of the invention set forth above is practiced with the proviso that if the opioid receptor is antagonized using naltrexone, then release of α-MSH is not stimulated with fluoxetine. However, the combination of naltrexone with fluoxetine may be used to affect weight loss in individuals who wish to lose weight, whether or not they are clinically categorized as obese. These individuals may include those with BMI of greater than 25, or those individuals with BMI of less than 25 who still wish to lose additional weight. This particular combination may also be used for the treatment of general obesity. In certain embodiments, the individual who wishes to lose additional weight does not suffer from binge eating disorder.

In some embodiments, the treating step of the above method comprises administering to the individual a first compound and a second compound, where the first compound is an opioid antagonist and the second compound enhances α-MSH activity.

In some embodiments the first compound and the second compound are administered more or less simultaneously. In other embodiments the first compound is administered prior to the second compound. In yet other embodiments, the first compound is administered subsequent to the second compound.

In certain embodiments, the first compound and the second compound are administered individually. In other embodiments, the first compound and the second compound are covalently linked to each other such that they form a single chemical entity. The single chemical entity is then digested and is metabolized into two separate physiologically active chemical entities, one of which is the first compound and the other one is the second compound.

In some embodiments, the compositions of the present invention are a combination of the following compounds:
 a SSRI in combination with a dopamine reuptake inhibitor, a dopamine/norepinephrine reuptake inhibitor, a norepinephrine reuptake inhibitor, an opioid antagonist, a partial opioid agonist, GABA inhibitor, a peripherally acting weight loss agent such as metformin, or a peptide, such as PYY, $PYY_{3-36}$, or leptin;
 Serotonin in combination with a dopamine reuptake inhibitor, a dopamine/norepinephrine reuptake inhibitor, an opioid antagonist, a partial opioid agonist, or a GABA inhibitor;
 a dopamine reuptake inhibitor in combination with a norepinephrine reuptake inhibitor, a norepinephrine releaser, a norepinephrine agonist, an opioid antagonist, a partial opioid agonist, a GABA inhibitor, an adenosine compound, a cholinergic receptor antagonist, or a peptide, such as PYY, $PYY_{3-36}$, or leptin;
 a dopamine/norepinephrine reuptake inhibitor in combination with an opioid antagonist, a partial opioid agonist, a GABA inhibitor, or a peripherally acting weight loss agent such as metformin;
 a dopamine agonist in combination with an opioid antagonist, a partial opioid agonist, a GABA inhibitor, or a peptide, such as PYY, $PYY_{3-36}$, or leptin.

Examples of norepinephrine agonists include phendimetrazine and benzphetamine. Examples of adenosine compounds include all xanthine derivatives, such as adenosine, caffeine, theophylline, theobromine, and aminophylline. An example of acholinergic receptor antagonist is nicotine.

In another aspect, the present invention relates to a method of increasing satiety in an individual comprising identifying an individual in need thereof and treating that individual to antagonize opioid receptor activity and to enhance α-MSH activity.

In some embodiments, the treating step of the above method comprises administering to the individual a first compound and a second compound, where the first compound is an opioid antagonist and the second compound enhances α-MSH activity.

In some embodiments the first compound and the second compound are administered nearly simultaneously. In other embodiments the first compound is administered prior to the second compound. In yet other embodiments, the first compound is administered subsequent to the second compound.

In yet another aspect, the present invention relates to a method of suppressing the appetite of an individual comprising identifying an individual in need thereof and treating that individual to antagonize opioid receptor activity and to enhance α-MSH activity.

In some embodiments, the treating step of the above method comprises administering to the individual a first compound and a second compound, where the first compound is an opioid antagonist and the second compound enhances α-MSH activity.

In some embodiments the first compound and the second compound are administered nearly simultaneously. In other embodiments the first compound is administered prior to the second compound. In yet other embodiments, the first compound is administered subsequent to the second compound.

In another aspect, the present invention relates to a method of increasing energy expenditure in an individual comprising identifying an individual in need thereof and treating that individual to antagonize opioid receptor activity and to enhance α-MSH activity.

In some embodiments, the treating step of the above method comprises administering to the individual a first compound and a second compound, where the first compound is an opioid antagonist and the second compound enhances α-MSH activity.

In some embodiments the first compound and the second compound are administered nearly simultaneously. In other embodiments the first compound is administered prior to the second compound. In yet other embodiments, the first compound is administered subsequent to the second compound.

In certain embodiments disclosed herein, an individual is given a pharmaceutical composition comprising a combination of two or more compounds to affect weight loss. In some of these embodiments, each compound is a separate chemical entity. However, in other embodiments, the two compounds are joined together by a chemical linkage, such as a covalent bond, so that the two different compounds form separate parts of the same molecule. The chemical linkage is selected such that after entry into the body, the linkage is broken, such as by enzymatic action, acid hydrolysis, base hydrolysis, or the like, and the two separate compounds are then formed.

Thus, in another aspect, the present invention relates to synthetic routes to novel molecules in which an opioid antagonist is linked by a flexible linker to a selective serotonin reuptake inhibitor (SSRI).

Data from previous structure-activity relationship (SAR) studies within the family of μ opioid antagonists may be used as a guide to determine which antagonists to use and the optimal position or positions on the antagonist molecules to attach the tether such that potency and selectivity of the antagonist will remain high. Similarly, SAR data within the family of SSRIs may be used as a guide to determine which inhibitors to use and the optimal position or positions on the inhibitors to attach the tether such that potency and selectivity remain high. The tether or linker moiety is chosen from among those of demonstrated utility for linking bioactive molecules together. Disclosed herein are representative opioid antagonists, linkers and SSRI molecules that can be attached together in different combinations to form heterobivalent therapeutic molecules.

Structure-activity relationships of the opioid agonists and antagonists have been reviewed. See for example, Zimmerman, D. M.; Leander, J. D. *J. Med. Chem.* 1990, 33, 895; Portoghese, P. S. *J. Med. Chem.* 1992, 35, 1927; Carroll, F. I. *J. Med. Chem.* 2003, 46, 1. The opioid antagonists, nalmefene (1), naltrexone (2), naloxone (3) and naltrexamine (4) are thebaine-derived structures that share a common opiate-type template. 1-Subtype selective opioid antagonists are of considerable current interest as agents for the treatment of obesity (Glass, M. J.; Billington, C. J.; Levine, A. S. *Neuropeptides* 1999, 33, 350) and CNS disorders (Reneric, J. P.; Bouvard, M. P. *CNS Drugs* 1998, 10, 365).

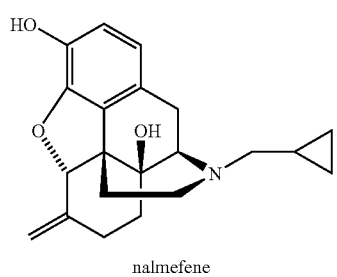

nalmefene

1

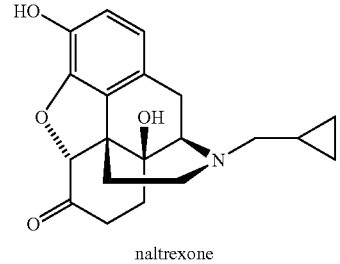

naltrexone

2

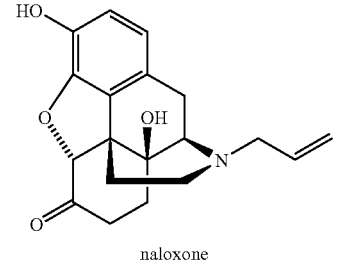

naloxone

3

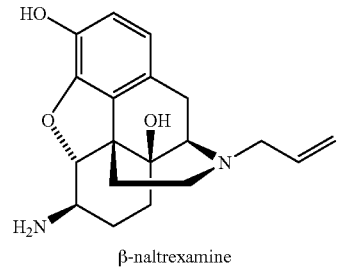

β-naltrexamine

4

N-Methyl and N-2-phenylethyl substituted opioids tend to show opioid agonist activity whereas N-allyl and N-cyclopropylmethyl substituted analogs tend to show opioid antagonist activity. Any N-attached linker moiety will be larger than methyl. Provided that the linker moiety does not mimic 2-phenylethyl, such linked opioids are expected to behave as opioid antagonists. Therefore, the nitrogen atom of nalmefene and naltrexone (and naloxone) is a suitable site for attachment of a linker moiety. Less SAR information is available with regard to substitution at other sites on these opioids, however, attachment of the linker unit to one or the other of the carbon atoms bearing one or more hydrogen atoms remains an option.

Both nalmefene and naltrexone are potent μ-opioid antagonists. The only structural difference is that nalmefene has a methylene group in place of the ketone oxygen atom in naltrexone. It is thus postulated that significant changes in structure at the ketone oxygen site in naltrexone do not significantly affect antagonist potency. Therefore, a linker may be attached to the methylene group in nalmefene without significant reduction in antagonist potency. Carbonyl derivatives of naloxone are well known and include symmetrical azine (=N—N=), mixed azine (Schmidhammer, H.; Kaspar, F.; Marki, A.; Borsodi, A. *Helv. Chim. Acta*

1994, 77, 999), hydazone (Hahn, E. F.; Itzhak, Y.; Nishimura, S.; Johnson, N.; Pasternak, G. W. *J. Pharm. Exper. Therapeutics* 1985, 235, 846-50), semicarbazone and thiosemicarbazone derivatives (Kolb, V. M.; Koman, A.; Neil, A. Pharmaceutical Res. 1985, 6, 266-71). Naloxazone, the hydrazone of naloxone, is an irreversible, selective and long acting antagonist of the µ-1 subclass of the opioid receptors (Pasternak, G. W.; Hahn, E. F. *J. of Med. Chem.* 1980, 23, 674-6). Certain of the derivatives are potent µ opioid antagonists while others are potent agonists.

Naltrexamine (4) has been linked by attachment of its primary amino group to a wide variety of other molecules producing, for example, a fluorogenic opioid receptor affinity label (Le Bourdonnec, B.; El Kouhen, R.; Lunzer, M. M.; Law, P. Y.; Loh, H. H.; Portoghese, P. S.; *J. Med. Chem.*; 2000; 43; 2489-2492), an extensive series of nonequilibrium opioid agonists and antagonists (Sayre, L. M.; Larson, D. L.; Takemori, A. E.; Portoghese, P. S. *J. Med. Chem.* 1984, 27, 1325), and a series of potent bivalent opioid antagonists (Erez, M.; Takemori, A. E.; Portoghese, P. S. *J. Med. Chem.* 1982, 25, 847-849). Consequently, the primary amino group of naltrexamine constitutes a suitable site for attachment of a linker moiety.

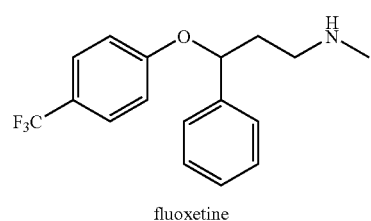

fluoxetine

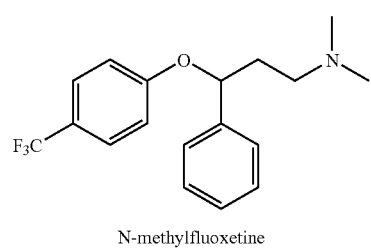

N-methylfluoxetine

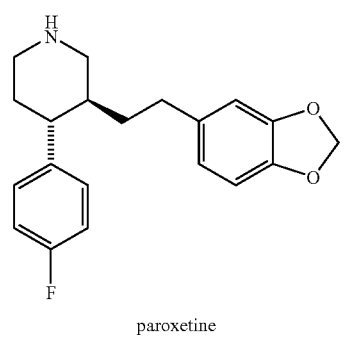

paroxetine

A limited SAR for fluoxetine (5) has been published in U.S. Pat. No. 4,214,081, incorporated by reference herein in its entirety. N-Methylfluoxetine (6) shows comparable potency and selectivity to that of fluoxetine toward inhibition of serotonin reuptake. Therefore, attachment of a linker to the nitrogen atom of fluoxetine can result in retention of the potency and selectivity of fluoxetine itself. However, the present disclosure is not limited to the fluoxetine series of SSRIs. It is envisaged that a variety of SSRI molecules such as paroxetine (Dechant, K. L.; Clissold, S. P. *Drugs*, 1991, 41, 225-253) or one or the other of the bivalent SSRIs described by Kozikowski et al. (Tamiz, A. P.; Zhang, J.; Zhang, M.; Wang, C. Z.; Johnson, K. M.; Kozikowski, A. P. *J. Am. Chem. Soc.* 2000, 122, 5393-5394; Tamiz, A. P.; Bandyopadhyay, B. C.; Zhang, J.; Flippen-Anderson, J. L.; Zhang, M.; Wang, C. Z.; Johnson, K. M.; Tella, S.; Kozikowski, A. P. *J. Med. Chem.* 2001, 44, 1615-1622) may also be utilized to construct the heterobivalent therapeutic molecules of this invention.

Examples of linkers reported in the scientific literature include methylene $(CH_2)_n$ linkers (Hussey, S. L.; Muddana, S. S.; Peterson, B. R.; *J. Am. Chem. Soc.* 2003; 125; 3692-3693; Tamiz, A. P.; Bandyopadhyay, B. C.; Zhang, J.; Flippen-Anderson, J. L.; Zhang, M.; Wang, C. Z; Johnson, K. M.; Tellar, S.; Kozikowski, A. P. *J. Med. Chem.* 2001, 44, 1615-1622), oligo ethyleneoxy $O(—CH_2CH_2O—)_n$ units used to link naltrexamine to other opioids, glycine oligomers of the formula $—NH—(COCH_2NH)_nCOCH_2CH_2CO—(NHCH_2CO)_nNH—$ used to link opioid antagonists and agonists together ((a) Portoghese, P. S.; Ronsisvalle, G.; Larson, D. L.; Yim, C. B.; Sayre, L. M.; Takemori, A. E. *Life Sci.* 1982, 31, 1283-1286. (b) Portoghese, P. S.; Larson, D. L.; Sayre, L. M.; Yim, C. B.; Ronsisvalle, G.; Tam, S. W.; Takemori, A. E. *J. Med. Chem.* 1986, 29, 1855-1861), hydrophilic diamines used to link opioid peptides together (Stepinski, J.; Zajaczkowski, I.; Kazem-Bek, D.; Temeriusz, A.; Lipkowski, A. W.; Tam, S. W. Internat. J. of Peptide & Protein Res. 1991, 38, 588-92), rigid double stranded DNA spacers (Paar, J. M.; Harris, N. T.; Holowka, D.; Baird, B. *J. Immunol.* 2002, 169, 856-864) and the biodegradable linker poly (L-lactic acid) (Klok, H.-A.; Hwang, J. J.; Iyer, S. N.; Stupp, S. I. *Macromolecules* 2002, 35, 746-759). The attachment of the tether to the antagonist can result in the antagonist achieving a favorable binding orientation. The linker itself may or may not be biodegradable. The linker may take the form of a prodrug and be tunable for optimal release kinetics of the linked drugs. The linker may be either conformationally flexible throughout its entire length or else a segment of the tether may be designed to be conformationally restricted (Portoghese, P. S.; Ronsisvalle, G.; Larson, D. L.; Takemori, A. E. *J. Med. Chem.* 1986, 29, 1650-1653).

In Scheme 1 below, naltrexone (2) is used in the linking reaction. As a consequence of the Wittig reaction, a double bond replaces the carbonyl group in naltrexone. The net result is fluoxetine linked with a flexible methylene linker to a nalmefene molecule by way of the nalmefene double bond.

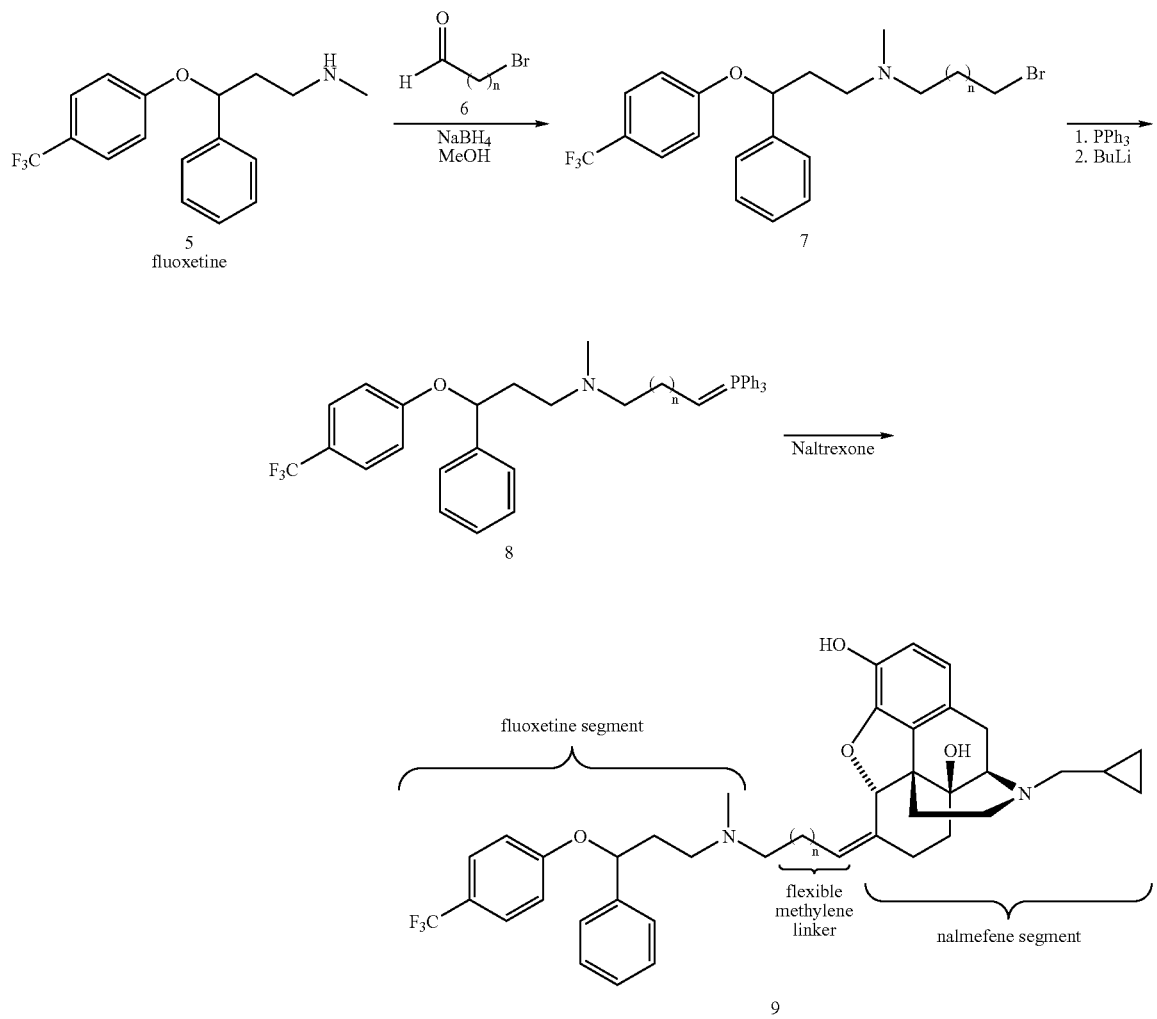

Scheme 1

Reductive amination of fluoxetine with an ω-bromoaldehyde such as 11-bromoundecanal 6 (n=9) gives bromoamine 7 (n=9), best stored as the hydrobromide salt to prevent an unwanted slow macrocyclization side reaction by way of attack of the free amino group on the carbon bearing the bromine atom. Reaction of 7 with triphenylphosphine gives the intermediate phosphonium salt, which upon rection with butyllithium generates the corresponding ylid 8 (n=9). A Wittig reaction between 8 and the ketone group of naltrexone (2) gives the linked molecule 9 containing a fluoxetine unit coupled to what is now a nalmefene unit. The expected mixture of cis, trans isomers about the newly introduced double bond is separable by standard chromatographic techniques. If racemic fluoxetine is used, then a mixture of two optically active diastereomers of 9 will be produced owing to the fact that a single enantiomer 2 of naltrexone was used. Chemists skilled in the art will recognize that the $(CH_2)_9$ linker may be varied in length and/or contain substituents by beginning with a different bromoaldehyde. Thus, pharmacological properties may be optimized. Molecule 9 is stable under physiological conditions. Opioid antagonist activity will be due to the covalently linked nalmefene unit and not due to free nalmefene released as a result of some cleavage reaction. Similarly, SSRI activity will be due to the covalently linked fluoxetine unit and not due to free fluoxetine released as a result of some cleavage reaction.

An analogous reaction sequence may be used in which the bromoaldehyde is derived from an oligo ethylene glycol as shown in Scheme 2 below. For example, tetraethylene glycol (10 n=2) is converted into bromide 11 (n=2), which is then oxidized under Swern conditions to aldehyde 12 (n=2). Substitution of aldehyde 12 for aldehyde 6 in Scheme 1 will give a series of irreversibly linked molecules in which the linker is more hydrophilic than that in molecules 9. Generation of the ylid in the oligo ethylene glycol series and the subsequent Wittig reaction is performed at reduced temperature to avoid β-elimination of the alkoxy group. If racemic fluoxetine is used, then a mixture of two optically active diastereomers of 13 will be produced owing to the fact that a single enantiomer 2 of naltrexone was used. Chemists skilled in the art will recognize that the $(OCH_2CH_2)_n$ linker may be varied in length by beginning with a different bromoaldehyde 12. Thus, pharmacological properties may be optimized. Molecule 13 is stable under physiological conditions.

Scheme 2

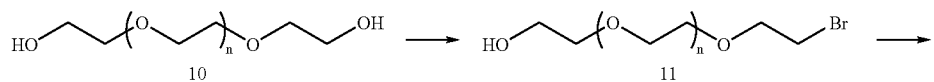

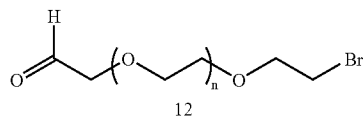

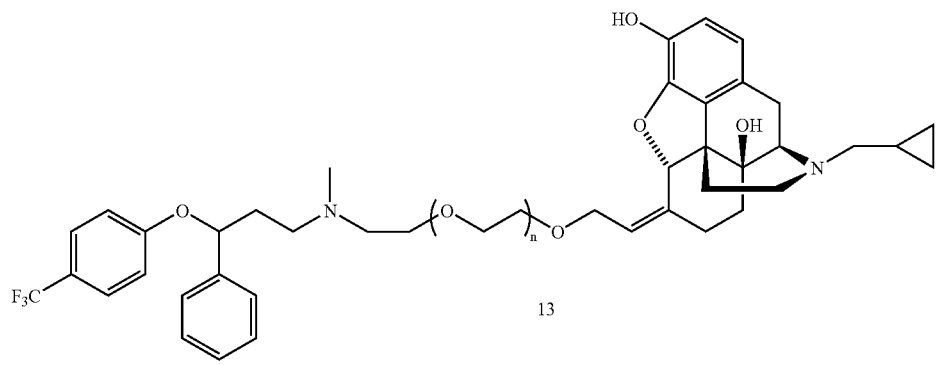

In Scheme 3, another linking method beginning with tetraethylene glycol is illustrated as an example of a variety of oligo ethylene glycols that may be used. Adapting the chemistry of Sashiwa et al. (Sashiwa, H.; Shigemasa, Y.; Roy, R. *Macromolecules* 2000, 33, 6913), tetraethylene glycol may be converted into acetal 14 (n=2) and subsequently into aldehyde 15. Reductive amination of fluoxetine with aldehyde 15 gives the fluoxetine derivative 16. Reduction of azide 16 to amine 17 and then reductive amination with naltrexone gives molecule 18 in which a fluoxetine unit is linked irreversibly by a flexible oligo ethyleneoxy unit to β-naltrexamine (after separation of the α and β isomers). If racemic fluoxetine is used, then a mixture of two optically active diastereomers of 18 will be produced owing to the fact that a single enantiomer 2 of naltrexone was used. Chemists skilled in the art will recognize that the $(OCH_2CH_2)_n$ linker may be varied in length by beginning with a different oligo ethylene glycol 10. Thus, pharmacological properties may be optimized. Molecule 18 should be stable under physiological conditions.

Scheme 3

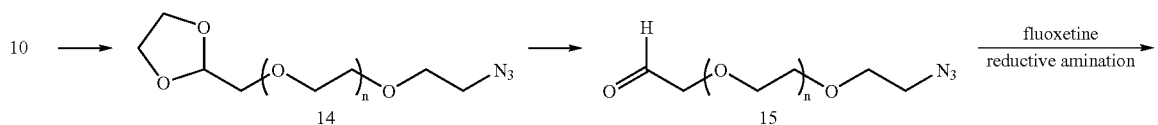

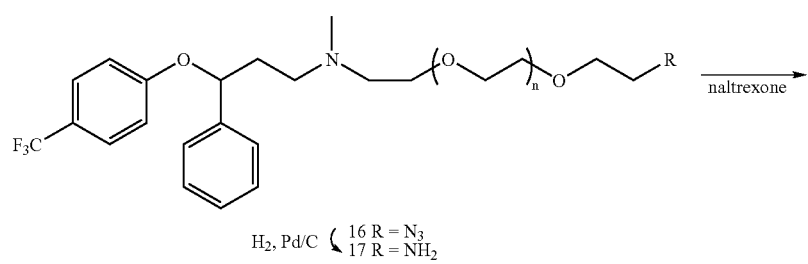

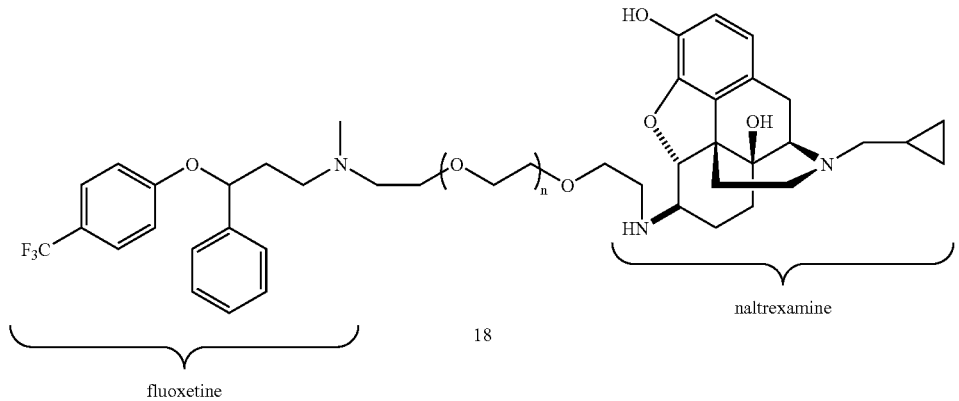

18 fluoxetine · naltrexamine

Scheme 4 illustrates a synthetic route to fluoxetine linked to nalmefene by way of the N-cyclopropyl group of nalmefene. The readily available t-butyldimethylsilyl protected noroxymorphone (19) is synthesized from morphine (Ninan, A.; Sainsbury, M. *Tetrahedron* 1992, 48, 6709-16), and then subjected to a reductive amination reaction with the commercially available cyclopropanecarboxaldehyde 20 (Aldrich, largely trans) giving ester 21. Wittig methyleneation gives ester 22, which is hydrolyzed to give acid 23. Activation of acid 23 with an appropriate carbodiimide and then N-acylation of fluoxetine derivative 17 (Scheme 3) gives 25, deprotection of which with $Bu_4NF$ gives the novel molecule 26. Chemists skilled in the art will recognize that the $(OCH_2CH_2)_n$ linker may be varied in length by beginning with a different aldehyde azide 15 in the synthesis of 17. Thus, pharmacological properties may be optimized. Molecule 26 should be stable under physiological conditions.

Alternatively, ester 22 may be reduced to aldehyde 24 using DIBAL at −78° C. Reductive amination of aldehyde 24 with amine 17 gives molecule 27 after removal of the TBDMS protecting group. Chemists skilled in the art will recognize that the $(OCH_2CH_2)_n$ linker may be varied in length by beginning with a different aldehyde azide 15 in the synthesis of 17. Thus, pharmacological properties may be optimized. Molecule 27 should be stable under physiological conditions.

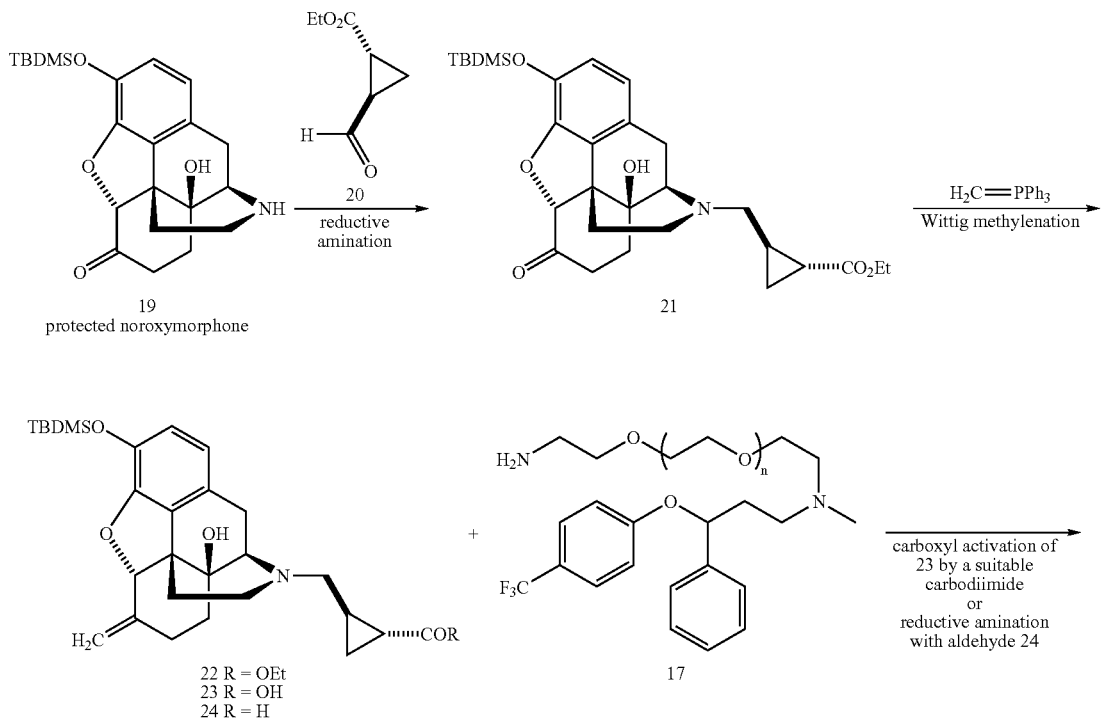

Scheme 4

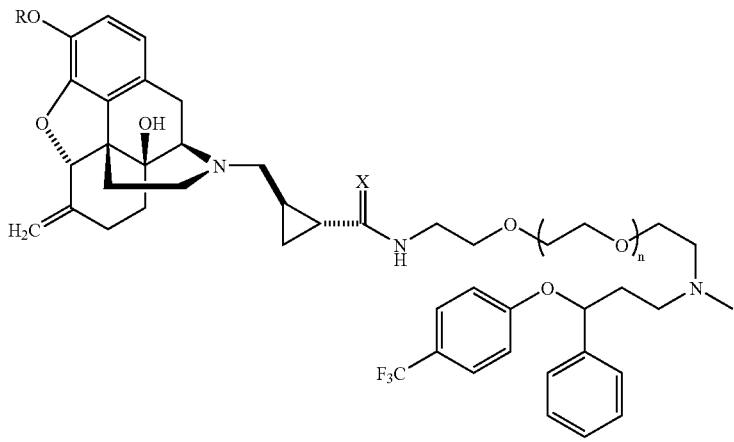

25 R = TBDMS, X = O
26 R = H, X = O
27 R = H, X = H, H

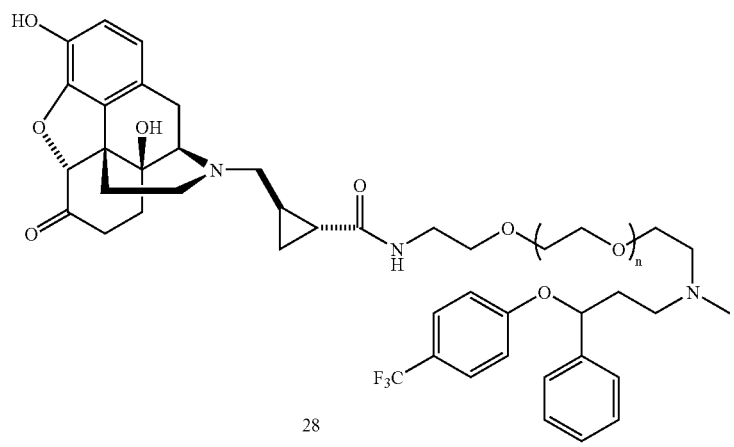

28

If the Wittig methyleneation step is omitted in the above sequence, then an analog of 26, namely ketone 28, is formed in which the methylene group of 26 is replaced by a carbonyl group. The result is a naltrexone unit linked to a fluoxetine unit by way of a flexible, hydrophilic $(CH_2CH_2O)_n$ linker in the form of compound 28. Chemists skilled in the art will recognize that the $(OCH_2CH_2)_n$ linker may be varied in length by beginning with a different aldehyde azide 15 in the synthesis of 17. Thus, pharmacological properties may be optimized. Molecule 28 is stable under physiological conditions.

Scheme 5 illustrates how fluoxetine may be linked to β-naltrexamine using a combination of linkers, namely the flexible glycine-based linkers 29 exploited by Portoghese et al. and the oligo ethylene glycol linkers used in the schemes above. Thus carboxyl activation of 29 with a suitable carbodiimide followed by monocondensation with β-naltrexamine gives amide 30. Reactivation of 30 followed by condensation with amine 17 (Scheme 3) gives molecule 31. Portoghese reports that symmetrical amides derived from linker 29 and β-naltrexamine are effective µ-opioid receptor antagonists. Chemists skilled in the art will recognize that the $—NH—(COCH_2NH)_{n-1}COCH_2CH_2CO—(NHCH_2CO)_nNH—$ linker may be varied in length by beginning with a different glycine-based linking unit 29 in the synthesis of 30. Thus, pharmacological properties may be optimized. Molecule 31 is stable under physiological conditions.

Scheme 5
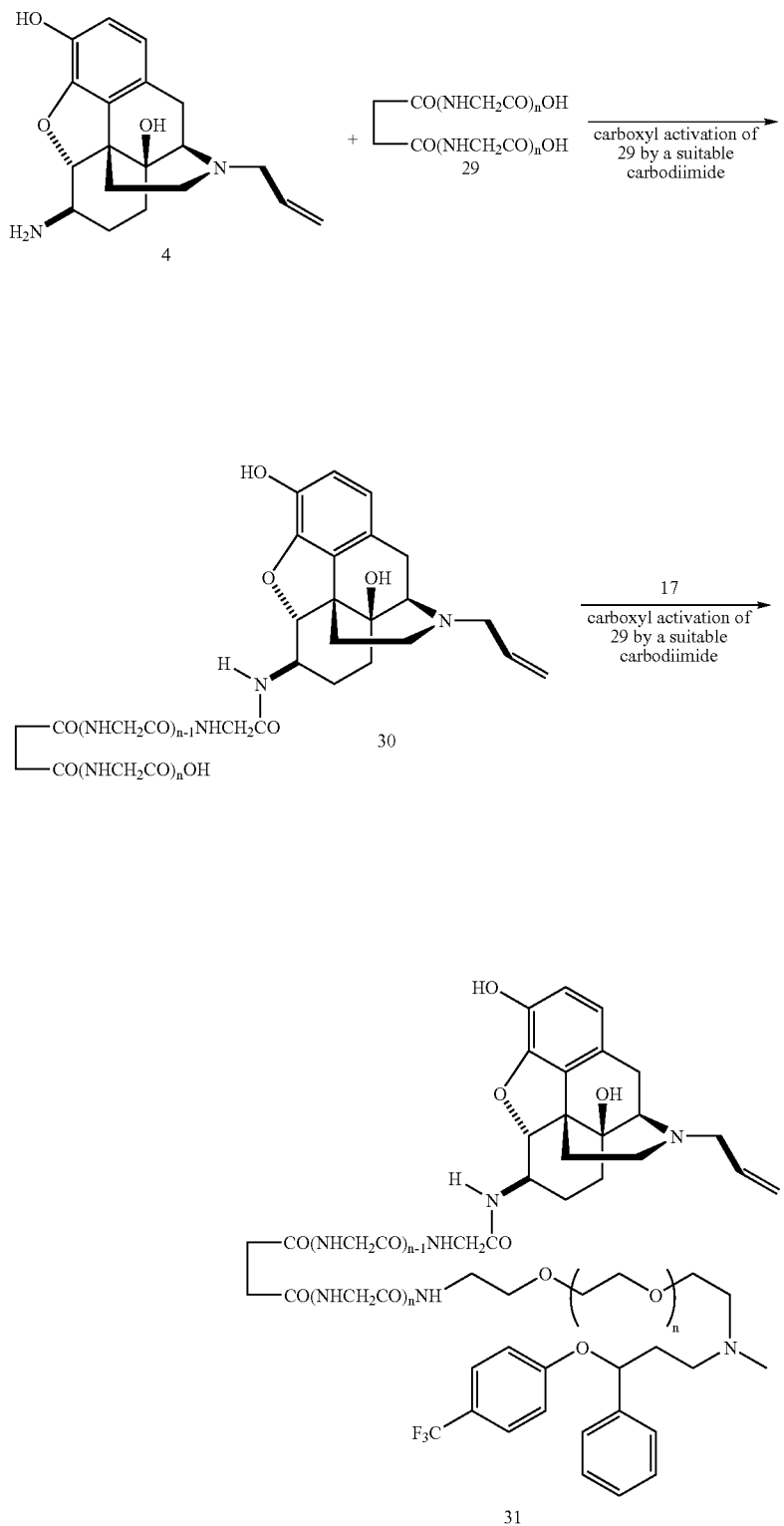
Reaction of bromide 7 (Scheme 1) with Mg in dry THF will give Grignard reagent 32, reaction of which with the carbonyl group of naltrexone gives adduct 33 after separation of the two diastereomers produced at the newly created chiral center. Adduct 33 contains a fluoxetine segment linked to a N-cyclopropylmethyl-normorphine unit by way of a flexible methylene linker. Chemists skilled in the art will recognize that the $(CH_2)_9$ linker may be varied in length by beginning with a different bromoaldehyde for the synthesis of bromide 7. Thus, pharmacological properties may be optimized. Molecule 33 is stable under physiological conditions.

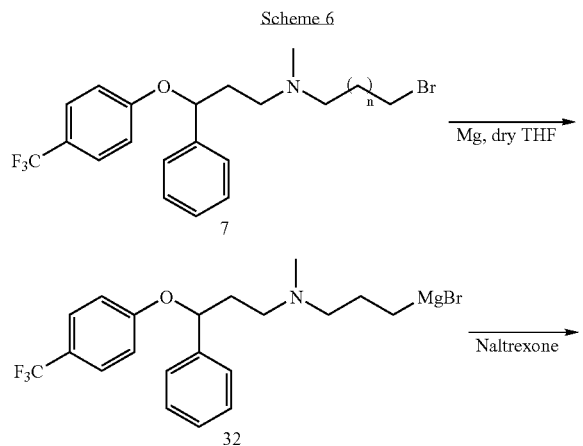

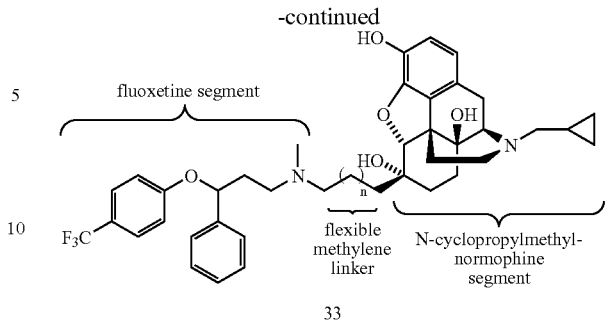

Throughout the above schemes, one should be able to employ N-desmethylfluoxetine (34), or any other derivative of fluoxetine, in place of fluoxetine. The resulting linked fluoxetine unit is identical to that of fluoxetine itself except that the methyl group of fluoxetine is replaced by a longer chain that is part of the linker. When necessary due to the use of strongly basic reagents or when chemoselectivity toward a primary amino group elsewhere in the molecule is required, one may protect the intermediate fluoxetine secondary amino group by use of the N-[2-(trimethylsilyl)ethoxy]methyl (SEM) group (Zeng, Z.; Zimmerman, S. C. *Tetrahedron Lett.* 1988, 29, 5123) as illustrated in Scheme 7.

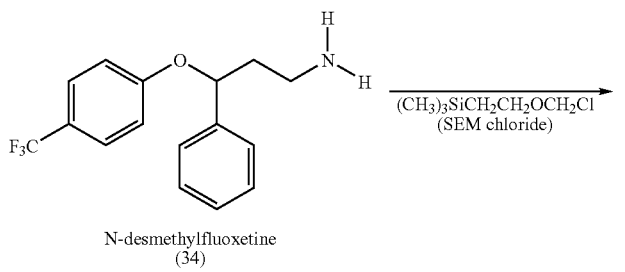

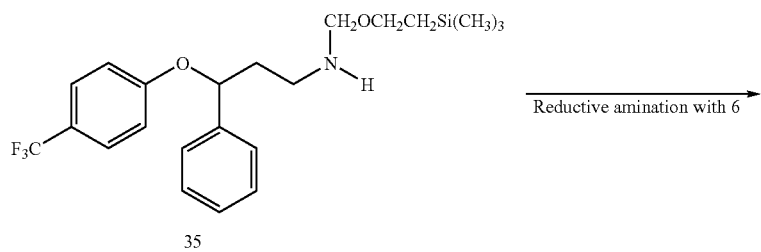

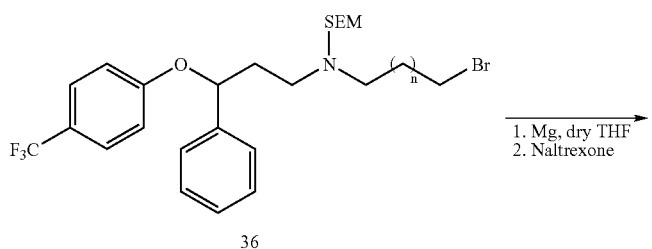

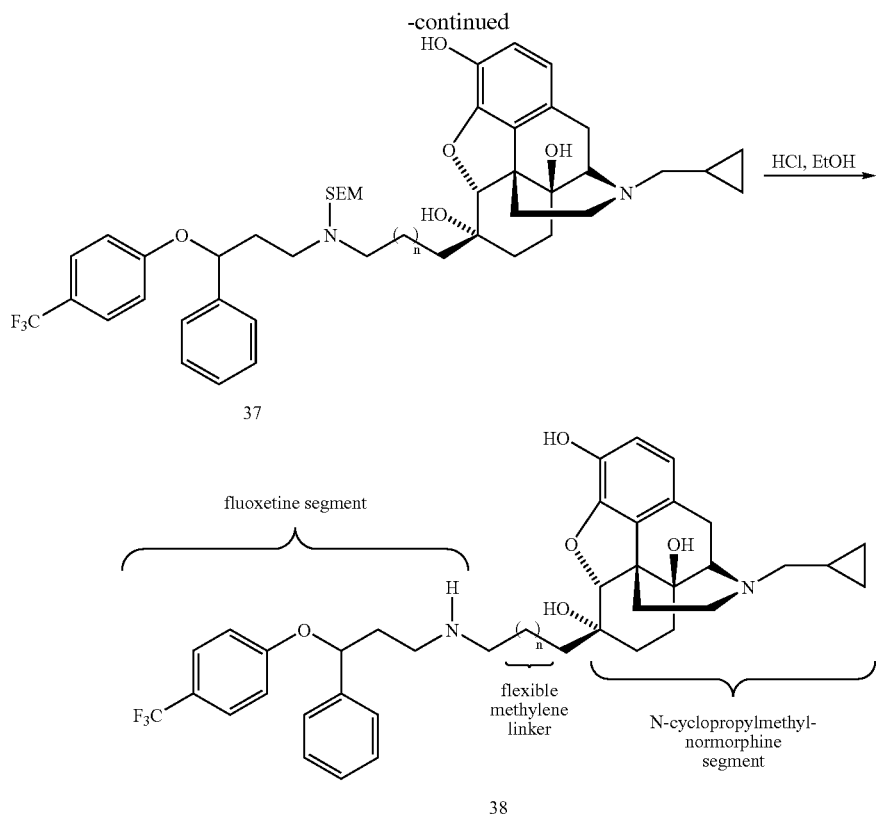

37

38

In another aspect, the invention relates to a pharmaceutical composition comprising a combination of an opioid antagonist and a compound that causes increased agonism of a melanocortin 3 receptor (MC3-R) or a melanocortin 4 receptor (MC4-R) compared to normal physiological conditions, as described above, or comprising a linked molecule, as described herein, and a physiologically acceptable carrier, diluent, or excipient, or a combination thereof.

The term "pharmaceutical composition" refers to a mixture of a compound of the invention with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

The term "physiologically acceptable" defines a carrier or diluent that does not abrogate the biological activity and properties of the compound.

The pharmaceutical compositions described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., 18th edition, 1990.

Suitable routes of administration may, for example, include oral, rectal, transmucosal, or intestinal administration; parenteral delivery, including intramuscular, subcutaneous, intravenous, intramedullary injections, as well as intrathecal, direct intraventricular, intraperitoneal, intranasal, or intraocular injections.

Alternately, one may administer the compound in a local rather than systemic manner, for example, via injection of the compound directly in the renal or cardiac area, often in a depot or sustained release formulation. Furthermore, one may administer the drug in a targeted drug delivery system, for example, in a liposome coated with a tissue-specific antibody. The liposomes will be targeted to and taken up selectively by the organ.

The pharmaceutical compositions of the present invention may be manufactured in a manner that is itself known, e.g., by means of conventional mixing, dissolving, granulating, dragee-making, levigating, emulsifying, encapsulating, entrapping or tabletting processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by mixing one or more solid excipient with pharmaceutical combination of the invention, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Many of the compounds used in the pharmaceutical combinations of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free acid or base forms.

Pharmaceutical compositions suitable for use in the present invention include compositions where the active ingredients are contained in an amount effective to achieve its intended purpose. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

The exact formulation, route of administration and dosage for the pharmaceutical compositions of the present invention can be chosen by the individual physician in view of the patient's condition. (See e.g., Fingl et al. 1975, in "The Pharmacological Basis of Therapeutics", Ch. 1 p. 1). Typically, the dose range of the composition administered to the patient can be from about 0.5 to 1000 mg/kg of the patient's body weight. The dosage may be a single one or a series of two or more given in the course of one or more days, as is needed by the patient. Note that for almost all of the specific compounds mentioned in the present disclosure, human dosages for treatment of at least some condition have been established. Thus, in most instances, the present invention will use those same dosages, or dosages that are between about 0.1% and 500%, more preferably between about 25% and 250% of the established human dosage. Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals.

Although the exact dosage will be determined on a drug-by-drug basis, in most cases, some generalizations regarding the dosage can be made. The daily dosage regimen for an adult human patient may be, for example, an oral dose of between 0.1 mg and 500 mg of each ingredient, preferably between 1 mg and 250 mg, e.g. 5 to 200 mg or an intravenous, subcutaneous, or intramuscular dose of each ingredient between 0.01 mg and 100 mg, preferably between 0.1 mg and 60 mg, e.g. 1 to 40 mg of each ingredient of the pharmaceutical compositions of the present invention or a pharmaceutically acceptable salt thereof calculated as the free base, the composition being administered 1 to 4 times per day. Alternatively the compositions of the invention may be administered by continuous intravenous infusion, preferably at a dose of each ingredient up to 400 mg per day. Thus, the total daily dosage by oral administration of each ingredient will typically be in the range 1 to 2000 mg and the total daily dosage by parenteral administration will typically be in the range 0.1 to 400 mg. Suitably the compounds will be administered for a period of continuous therapy, for example for a week or more, or for months or years.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen which maintains plasma levels above the MEC for 10-90% of the time, preferably between 30-90% and most preferably between 50-90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound of the invention formulated in a compatible pharmaceutical carrier may also be prepared, placed in an appropriate container, and labeled for treatment of an indicated condition.

It will be understood by those of skill in the art that numerous and various modifications can be made without departing from the spirit of the present invention. Therefore, it should be clearly understood that the forms of the present invention are illustrative only and are not intended to limit the scope of the present invention.

Some Embodiments of the Invention

Some of the embodiments of the present invention are as follows:

In the first embodiment, the invention relates to a composition for affecting weight loss comprising a first compound and a second compound, wherein said first compound is an opioid antagonist and said second compound causes increased agonism of a melanocortin 3 receptor (MC3-R) or a melanocortin 4 receptor (MC4-R) compared to normal physiological conditions.

In the second embodiment, the invention relates to the composition of the first embodiment, wherein said opioid antagonist antagonizes an opioid receptor in a mammal.

In the third embodiment, the invention relates to the composition of the second embodiment, wherein said opioid receptor is selected from a μ-opioid receptor (MOP-R), a η-opioid receptor, and a δ-opioid receptor.

In the fourth embodiment, the invention relates to the composition of the second embodiment, wherein said opioid antagonist antagonizes a μ-opioid receptor (MOP-R) in a mammal.

In the fifth embodiment, the invention relates to the composition of the first embodiment, wherein said opioid antagonist is selected from the group consisting of alvimopan, norbinaltorphimine, nalmefene, naloxone, naltrexone, methylnaltrexone, and nalorphine, and pharmaceutically acceptable salts or prodrugs thereof.

In the sixth embodiment, the invention relates to the composition of the first embodiment, wherein said opioid antagonist is a partial opioid agonist.

In the seventh embodiment, the invention relates to the composition of the sixth embodiment, wherein said partial opioid agonist is selected from the group consisting of pentacozine, buprenorphine, nalorphine, propiram, and lofexidine.

In the eighth embodiment, the invention relates to the composition of the first embodiment, wherein said second compound triggers the release of α-melanocyte stimulating hormone (α-MSH).

In the ninth embodiment, the invention relates to the composition of the eighth embodiment, wherein said second compound increases the extracellular serotonin concentrations in the hypothalamus.

In the tenth embodiment, the invention relates to the composition of the ninth embodiment, wherein said second compound is selected from the group consisting of a selective serotonin reuptake inhibitor (SSRI), a serotonin 2C agonist, and a serotonin 1B agonist.

In the eleventh embodiment, the invention relates to the composition of the tenth embodiment, wherein said second compound is selected from the group consisting of fluoxetine, fluvoxamine, sertraline, paroxetine, citalopram, escitalopram, sibutramine, duloxetine, and venlafaxine, and pharmaceutically acceptable salts or prodrugs thereof.

In the twelfth embodiment, the invention relates to the composition of the first embodiment, wherein said second compound suppresses the expression of the AgRP gene or the production or release of agouti-related protein (AgRP).

In the thirteenth embodiment, the invention relates to the composition of the first embodiment, wherein said second compound suppresses the activity of neurons that express AgRP.

In the fourteenth embodiment, the invention relates to the composition of the first embodiment, wherein said second compound suppresses the expression of the NPY gene or the production or release of neuropeptide Y (NPY).

In the fifteenth embodiment, the invention relates to the composition of the first embodiment, wherein said second compound suppresses the activity of neurons that express NPY.

In the sixteenth embodiment, the invention relates to the composition of the first embodiment, wherein said second compound is selected from the group consisting of NPY Y1 receptor antagonists, ghrelin antagonists, and leptin.

In the seventeenth embodiment, the invention relates to the composition of the first embodiment, wherein said second compound agonizes NPY Y2 receptor.

In the eighteenth embodiment, the invention relates to the composition of the first embodiment, wherein said second compound is selected from the group consisting of a γ-amino butyric acid (GABA) inhibitor, a GABA receptor antagonist, and a GABA channel antagonist.

In the nineteenth embodiment, the invention relates to the composition of the eighteenth embodiment, wherein said GABA inhibitor is a 5-HT1b agonist, which may be selected from sumatriptan, almotriptan, naratriptan, frovatriptan, rizatriptan, zomitriptan, and elitriptan.

In the twentieth embodiment, the invention relates to the composition of the eighteenth embodiment, wherein said GABA inhibitor suppresses the expression of the AgRP gene.

In the twenty first embodiment, the invention relates to the composition of the eighteenth embodiment, wherein said GABA inhibitor suppresses the production or release of AgRP.

In the twenty second embodiment, the invention relates to the composition of the eighteenth embodiment, wherein said GABA inhibitor increases the expression of the POMC gene.

In the twenty third embodiment, the invention relates to the composition of the eighteenth embodiment, wherein said GABA inhibitor increases the production or release of α-MSH from pro-opiomelanocortin (POMC) neurons.

In the twenty fourth embodiment, the invention relates to the composition of the eighteenth embodiment, wherein said GABA inhibitor increases the activity of POMC expressing neurons.

In the twenty fifth embodiment, the invention relates to the composition of the eighteenth embodiment, wherein the GABA inhibitor is topiramate.

In the twenty sixth embodiment, the invention relates to the composition of the first embodiment, wherein said second compound is a dopamine reuptake inhibitor.

In the twenty seventh embodiment, the invention relates to the composition of the twenty sixth embodiment, wherein said dopamine reuptake inhibitor is phentermine.

In the twenty eighth embodiment, the invention relates to the composition of the first embodiment, wherein said second compound is a norepinephrine reuptake inhibitor.

In the twenty ninth embodiment, the invention relates to the composition of the twenty eighth embodiment, wherein said norepinephrine reuptake inhibitor is selected from bupropion, thionisoxetine, and reboxetine.

In the thirtieth embodiment, the invention relates to the composition of the first embodiment, wherein said second compound is a dopamine agonist.

In the thirty first embodiment, the invention relates to the composition of the thirtieth embodiment, wherein said dopamine agonist is selected from the group consisting of cabergoline, amantadine, lisuride, pergolide, ropinirole, pramipexole, and bromocriptine.

In the thirty second embodiment, the invention relates to the composition of the first embodiment, wherein said second compound is a norepinephrine releaser.

In the thirty third embodiment, the invention relates to the composition of the thirty second embodiment, wherein said norepinephrine releaser is diethylpropion.

In the thirty fourth embodiment, the invention relates to the composition of the first embodiment, wherein said second compound is a combination of a dopamine reuptake inhibitor and a norepinephrine reuptake inhibitor.

In the thirty fifth embodiment, the invention relates to the composition of the thirty fourth embodiment, wherein said second compound is selected from bupropion and mazindol.

In the thirty sixth embodiment, the invention relates to the composition of the first embodiment, wherein said second compound is a combination of a SSRI and a norepinephrine reuptake inhibitor.

In the thirty seventh embodiment, the invention relates to the composition of the thirty sixth embodiment, wherein said second compound is selected from sibutramine, venlafaxine, and duloxetine.

In the thirty eighth embodiment, the invention relates to the composition of the first embodiment, wherein said first compound is naltrexone and said second compound is fluoxetine.

In the thirty ninth embodiment, the invention relates to the composition of the thirty eighth embodiment, wherein the naltrexone is in a time-release formulation whereas the fluoxetine is in an immediate release formulation.

In the fortieth embodiment, the invention relates to a method of affecting weight loss, comprising identifying an individual in need thereof and treating that individual to antagonize opioid receptor activity and to enhance α-MSH activity.

In the forty first embodiment, the invention relates to the method of the fortieth embodiment, wherein said individual has a body mass index greater than 25.

In the forty second embodiment, the invention relates to the method of the fortieth embodiment, wherein opioid receptor activity is antagonized by administering an opioid receptor antagonist.

In the forty third embodiment, the invention relates to the method of the forty second embodiment, wherein the opioid receptor antagonist is a MOP receptor antagonist.

In the forty fourth embodiment, the invention relates to the method of the fortieth embodiment, wherein the opioid receptor antagonist is selected from alvimopan, norbinaltorphimine, nalmefene, naloxone, naltrexone, methylnaltrexone, and nalorphine, and pharmaceutically acceptable salts or prodrugs thereof.

In the forty fifth embodiment, the invention relates to the method of the forty second embodiment, wherein said opioid receptor antagonist is a partial opioid agonist.

In the forty sixth embodiment, the invention relates to the method of the forty fifth embodiment, wherein said partial opioid agonist is selected from the group consisting of pentacozine, buprenorphine, nalorphine, propiram, and lofexidine.

In the forty seventh embodiment, the invention relates to the method of the fortieth embodiment through the forty fifth embodiment, wherein α-MSH activity is enhanced by administering a compound, wherein said compound triggers release of α-MSH or increases the activity of neurons that express α-MSH.

In the forty eighth embodiment, the invention relates to the method of the forty seventh embodiment, wherein said compound is a selective serotonin reuptake inhibitor (SSRI) or a specific 5-HT receptor agonist.

In the forty ninth embodiment, the invention relates to the method of the forty eighth embodiment, wherein said 5-HT receptor is selected from 5-HT1b receptor and 5-HT2c receptor.

In the fiftieth embodiment, the invention relates to the method of the forty eighth embodiment, wherein said SSRI is selected from fluoxetine, fluvoxamine, sertraline, paroxetine, citalopram, escitalopram, sibutramine, duloxetine, and venlafaxine, and pharmaceutically acceptable salts or prodrugs thereof.

In the fifty first embodiment, the invention relates to the method of the forty seventh embodiment, wherein said compound is a γ-amino butyric acid (GABA) inhibitor.

In the fifty second embodiment, the invention relates to the method of the fifty first embodiment, wherein said GABA inhibitor is a 5-HT1b receptor agonist.

In the fifty third embodiment, the invention relates to the method of the fifty first embodiment, wherein said GABA inhibitor suppresses the expression of the AgRP gene.

In the fifty fourth embodiment, the invention relates to the method of the fifty first embodiment, wherein said GABA inhibitor suppresses the production or release of AgRP.

In the fifty fifth embodiment, the invention relates to the method of the forty eighth embodiment, wherein said 5-HT agonists inhibits the NPY/AgRP/GABA neurons.

In the fifty sixth embodiment, the invention relates to the method of the fifty first embodiment, wherein said GABA inhibitor suppresses the activity of neurons that express AgRP.

In the fifty seventh embodiment, the invention relates to the method of the fifty first embodiment, wherein said GABA inhibitor is topiramate.

In the fifty eighth embodiment, the invention relates to the method of the forty seventh embodiment, wherein said compound is selected from the group consisting of a dopamine reuptake inhibitor, a norepinephrine reuptake inhibitor, a dopamine agonist, a norepinephrine releaser, a combination of a dopamine reuptake inhibitor and a norepinephrine reuptake inhibitor, and a combination of a SSRI and a norepinephrine reuptake inhibitor.

In the fifty ninth embodiment, the invention relates to the method of the fifty eighth embodiment, wherein said compound is not phentermine.

In the sixtieth embodiment, the invention relates to the method of the fortieth embodiment, with the proviso that the individual is not suffering from Prader-Willi syndrome.

In the sixty first embodiment, the invention relates to the method of the fortieth embodiment, with the proviso that if the opioid receptor is antagonized using naltrexone, then release of α-MSH is not stimulated with fluoxetine.

In the sixty second embodiment, the invention relates to the method of the fortieth embodiment, wherein said treating step comprises administering to said individual a first compound and a second compound, wherein said first compound is an opioid antagonist and said second compound enhances α-MSH activity.

In the sixty third embodiment, the invention relates to the method of the sixty second embodiment, wherein said first compound and said second compound are administered nearly simultaneously.

In the sixty fourth embodiment, the invention relates to the method of the sixty third embodiment, wherein said first compound is administered prior to said second compound.

In the sixty fifth embodiment, the invention relates to the method of the sixty fourth embodiment, wherein said first compound is administered subsequent to said second compound.

In the sixty sixth embodiment, the invention relates to a method of increasing satiety in an individual comprising identifying an individual in need thereof and treating that individual to antagonize opioid receptor activity and to enhance α-MSH activity.

In the sixty seventh embodiment, the invention relates to the method of the sixty sixth embodiment, wherein said treating step comprises administering to said individual a first compound and a second compound, wherein said first compound is an opioid antagonist and said second compound enhances α-MSH activity.

In the sixty eighth embodiment, the invention relates to the method of the sixty seventh embodiment, wherein said first compound and said second compound are administered nearly simultaneously.

In the sixty ninth embodiment, the invention relates to the method of the sixty seventh embodiment, wherein said first compound is administered prior to said second compound.

In the seventieth embodiment, the invention relates to the method of the sixty seventh embodiment, wherein said first compound is administered subsequent to said second compound.

In the seventy first embodiment, the invention relates to a method of increasing energy expenditure in an individual comprising identifying an individual in need thereof and treating that individual to antagonize opioid receptor activity and to enhance α-MSH activity.

In the seventy second embodiment, the invention relates to the method of the seventy first embodiment, wherein said treating step comprises administering to said individual a first compound and a second compound, wherein said first compound is an opioid antagonist and said second compound enhances α-MSH activity.

In the seventy third embodiment, the invention relates to the method of the seventy second embodiment, wherein said first compound and said second compound are administered nearly simultaneously.

In the seventy fourth embodiment, the invention relates to the method of the seventy second embodiment, wherein said first compound is administered prior to said second compound.

In the seventy fifth embodiment, the invention relates to the method of the seventy second embodiment, wherein said first compound is administered subsequent to said second compound.

In the seventy sixth embodiment, the invention relates to a method of suppressing the appetite of an individual comprising identifying an individual in need thereof and treating that individual to antagonize opioid receptor activity and to enhance α-MSH activity.

In the seventy seventh embodiment, the invention relates to the method of the seventy sixth embodiment, wherein said treating step comprises administering to said individual a first compound and a second compound, wherein said first compound is an opioid antagonist and said second compound enhances α-MSH activity.

In the seventy eighth embodiment, the invention relates to the method of the seventy seventh embodiment, wherein said first compound and said second compound are administered nearly simultaneously.

In the seventy ninth embodiment, the invention relates to the method of the seventy seventh embodiment, wherein said first compound is administered prior to said second compound.

In the eightieth embodiment, the invention relates to the method of the seventy seventh embodiment, wherein said first compound is administered subsequent to said second compound.

In the eighty first embodiment, the invention relates to a method of affecting weight loss in an individual comprising identifying an individual in need thereof and treating that individual with a combination of naltrexone and fluoxetine, provided that the individual does not suffer from Prader-Willi syndrome or binge eating disorder.

In the eighty second embodiment, the invention relates to the method of the eighty first embodiment, wherein the individual has a BMI greater than 30.

In the eighty third embodiment, the invention relates to the method of the eighty first embodiment, wherein the individual has a BMI greater than 25.

In the eighty fourth embodiment, the invention relates to the method of the eighty first embodiment, wherein the naltrexone is in a time-release formulation whereas the fluoxetine is in an immediate release formulation.

In the eighty fifth embodiment, the invention relates to the method of the eighty fourth embodiment, wherein the plasma concentration level of both naltrexone and fluoxetine follow a similar concentration profile.

In the eighty sixth embodiment, the invention relates to the method of the eighty fourth embodiment, wherein the naltrexone and the fluoxetine are administered substantially simultaneously.

In the eighty seventh embodiment, the invention relates to the method of the eighty fourth embodiment, wherein the naltrexone is administered prior to the fluoxetine.

In the eighty eighth embodiment, the invention relates to the method of the eighty fourth embodiment, wherein the naltrexone is administered subsequent to the fluoxetine.

EXAMPLES

The examples below are non-limiting and are merely representative of various aspects of the invention.

Example 1

Combination of Fluoxetine and Naltrexone

Individuals having a BMI of greater than 25 are identified. Each individual is instructed to take one 20 mg tablet of fluoxetine (PROZAC®) on a daily basis, in addition to one 50 mg tablet of naltrexone on a daily basis.

The individuals are monitored for a period of months. It is recommended that the dosage be adjusted so that each individual loses weight at a rate of 10% of initial weight every 6 months. However, the rate of weigh loss for each individual may be adjusted by the treating physician based on the individual's particular needs.

If the initial dosage is not effective, then the fluoxetine dosage can be increased by 20 mg per day, though never exceeding 80 mg total per day. If the initial dosage results in a more rapid weight loss than the above rate, the dosage of each of fluoxetine or naltrexone can be reduced.

Fluoxetine has a physiological half life of about 9 hours, whereas that of naltrexone is about 1.5 hours. Thus, in some cases, it is beneficial to administer one dose of fluoxetine per day in conjunction with two or three or more doses of naltrexone throughout the day. Naltrexone may also be in a time-release formulation where the dose is administered once a day, but naltrexone gradually enters the blood stream throughout the day, or in the course of a 12 hour period.

Example 2

Combination of Fluoxetine and Nalmefene

Individuals having a BMI of greater than 25 are identified. Each individual is instructed to take one 20 mg tablet of fluoxetine (PROZAC®) on a daily basis. In addition, each individual is injected with 1 mL of a solution of 100 μg of nalmefene in 1 mL of saline, intravenously, intramuscularly, or subcutaneously.

The individuals are monitored for a period of months. It is recommended that the dosage be adjusted so that each individual loses weight at a rate of 10% of initial weight every 6 months. However, the rate of weigh loss for each individual may be adjusted by the treating physician based on the individual's particular needs.

If the initial dosage is not effective, then the fluoxetine dosage can be increased by 20 mg per day, though never exceeding 80 mg total per day. In addition, the dosage of nalmefene may be increased up to 2 mL of a solution of 1 mg of nalmefene in 1 mL of saline. If the initial dosage results in a more rapid weight loss than the above rate, the dosage of each of fluoxetine or nalmefene can be reduced.

Example 3

Combination of Fluoxetine and Naloxone

Individuals having a BMI of greater than 25 are identified. Each individual is instructed to take one 20 mg tablet of fluoxetine (PROZAC®) on a daily basis. In addition, each individual is injected with 1 mL of a solution of 400 μg of naloxone in 1 mL of saline, intravenously, intramuscularly, or subcutaneously.

The individuals are monitored for a period of months. It is recommended that the dosage be adjusted so that each individual loses weight at a rate of 10% of initial weight every 6 months. However, the rate of weigh loss for each individual may be adjusted by the treating physician based on the individual's particular needs.

If the initial dosage is not effective, then the fluoxetine dosage can be increased by 20 mg per day, though never exceeding 80 mg total per day. If the initial dosage results in a more rapid weight loss than the above rate, the dosage of each of fluoxetine or nalmefene can be reduced.

Example 4

Combination of Opioid Antagonist and Sibutramine

Individuals having a BMI of greater than 25 are identified. Each individual is instructed to take nalmefene, naltrexone, or naloxone in the dosage set forth in Examples 1-3. In addition, each individual is instructed to take 10 mg of sibutramine orally once a day.

The individuals are monitored for a period of months. It is recommended that the dosage be adjusted so that each individual loses weight at a rate of 10% of initial weight every 6 months. However, the rate of weigh loss for each individual may be adjusted by the treating physician based on the individual's particular needs.

If the initial dosage is not effective, then the sibutramine dosage can be increased 15 mg per day. Dosages of sibutramine in excess of 15 mg per day are not recommended. If the initial dosage results in a more rapid weight loss than the above rate, the dosage of each of sibutramine, nalmefene, naltrexone, or naloxone can be reduced.

Example 5

Combination of Opioid Antagonist and Bupropion

Individuals having a BMI of greater than 25 are identified. Each individual is instructed to take nalmefene, naltrexone, or naloxone in the dosage set forth in Examples 1-3. In addition, each individual is instructed to take bupropion. The usual adult does is 300 mg per day, given three times daily. Dosing should begin at 200 mg per day, given as 100 mg twice daily. Based on clinical response, this dose may be increased to 300 mg per day, given as 100 mg three times daily. No single dose is to exceed 150 mg.

The individuals are monitored for a period of months. It is recommended that the dosage be adjusted so that each individual loses weight at a rate of 10% of initial weight every 6 months. However, the rate of weigh loss for each individual may be adjusted by the treating physician based on the individual's particular needs.

Example 6

Combination of Opioid Antagonist and Phentermine

Individuals having a BMI of greater than 25 are identified. Each individual is instructed to take nalmefene, naltrexone, or naloxone in the dosage set forth in Examples 1-3. In addition, each individual is instructed to take 37.5 mg of phentermine orally once a day.

The individuals are monitored for a period of months. It is recommended that the dosage be adjusted so that each individual loses weight at a rate of 10% of initial weight every 6 months. However, the rate of weigh loss for each individual may be adjusted by the treating physician based on the individual's particular needs.

Example 7

Combinations with Naltrexone

In a multicenter, randomized, blinded, placebo-controlled clinical trial with 6 groups, the following drug combinations are tested:

Group 1: Fluoxetine 60 mg po QD plus Naltrexone 50 mg po QD
Group 2: Fluoxetine 60 mg po QD plus N-placebo po QD
Group 3: Bupropion-SR 150 mg po BID plus Naltrexone 50 mg po QD
Group 4: Bupropion-SR 150 mg po BID plus N-placebo po QD
Group 5: P-placebo po BID plus Naltrexone 50 mg po QD
Group 6: P-placebo po BID plus N-placebo po QD In any of the above groups, the dosage of fluoxetine may be in the range between 6 mg and 60 mg, for example, 6 mg, 10 mg, 12 mg, 18 mg, 20 mg, 24 mg, 30 mg, 36 mg, 40 mg, 42 mg, 45 mg, 48 mg, 54 mg, and 60 mg. Bupropion may be administered in doses in the range between 30 mg and 300 mg, for example, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, and 300 mg. Naltrexone may be administered in doses in the range between 5 mg and 50 mg, for example, 5 mg, 10 mg, 15 mg, 20 mg, 25 mg, 30 mg, 35 mg, 40 mg, 45 mg, and 50 mg.

Subjects are evaluated as out-patients during this study. All subjects in this trial receive diet instruction, behavior modification advice and instruction to increase their activity, a regimen shown to give weight loss. Subjects are randomized to receive study drugs in various combinations.

Subjects in groups 5 and 6 cross-over to treatment with fluoxetine plus naltrexone or bupropion SR plus naltrexone after week 16 for the extension treatment period which provide additional data on safety of the combination therapies.

The primary endpoint is percent and absolute change from baseline in body weight at 16 weeks. Secondary endpoints include weight loss at 24, 36, and 48 weeks, number and proportion of subjects who achieve at least a 5% weight loss and a 10% weight loss (responder analysis), changes in obesity-associated cardiovascular risk factors (total cholesterol, LDL cholesterol, HDL cholesterol, triglycerides, glucose and insulin) and waist circumference, and safety and tolerability. Adverse events, laboratory parameters, vital signs, and the Hospital Anxiety and Depression (HAD) Scale are used to monitor safety and tolerability.

Example 8

Dose-Response Experiments

Seventy, four week old, male C57/B16J⁻ mice (Jackson Laboratory), 22-30 g were sham injected daily with 0.1 mL 0.9% saline (pH 7.4) for 1 week prior to the experiments. Animals were weighed and randomized to 1 of 7 weight-matched dose groups (0, 1.5, 3, 5.5, 10, 18, and 30 mg/kg; n=10/group for fluoxetine; 0, 1.5, 3, 5.5, 10, 18, and 30 mg/kg; n=3/group for naltrexone) the day before experiments began. Food was removed between 4:30-5:30 pm the day before the experiment. Animals received a 0.3 mL bolus (fluoxetine) or 0.1 mL bolus (naltrexone) intraperitoneal injection between 9-10:30 am, and food was provided immediately following injection. 3 animals/group received injections on each testing day (i.e., 3 runs of 3/group; 1 run of 1/group). Food was weighed 1, 2, 4, 8, and 24 h post-injection. Cumulative food intake±SEM was calculated and analyzed using Prizm. Doses were log transformed and fit to a sigmoidal curve, food intake was expressed as a proportion of the food intake in saline treated animals. From the curve, the $EC_{50}$ at each time point for each drug was determined.

Similar procedures as described above were followed using AM251 and nalmefene, fluvoxamine and nalmefene, and bupropion and naltrexone.

The results are set forth in the table below:

200 μm thick coronal slices were cut from the ARC of four-week old male POMC-EGFP mice. Slices were maintained in Krebs solution (NaCl (126 mM), KCl (2.5 mM), $MgCl_2$ 91.2 mM), $CaCl_2.2H_2O$ (2.4 mM), $NaH_2PO_4.H_2O$ (1.2 mM), $NaHCO_3$ (21.4 mM), glucose (11.1 mM)) at 35° C. and saturated with 95% $O_2$ and 5% $CO_2$ for 1 hr prior to recordings. Recordings were made in Krebs at 35° C. Slices were visualized on an Axioskop FS2 plus (Zeiss) through standard infra red optics and using epifluorescence through a FITC (longpass) filter set. POMC-EGFP neurons in hypothalamic slices had a resting membrane potential of −40 to −45 mV and exhibited frequent spontaneous action potentials. Cell-attached recordings were made from fluorescent neurons using an Axopatch 200B amplifier (Axon Instruments) and Clampex 8 (Axon Instruments). Action potentials frequencies were determined using an event detection program (Mini Analysis; Synaptosoft Inc., Decatur, Ga.). Drugs were applied to the bath for 3 min.

Data were analyzed by determining the average firing rate for 500 sec prior to drug addition, and analyzing treatments relative to this frequency (that is, firing rates were normalized to the pre-treatment frequency). The ratio's listed for the combinations are the ratio of the effect of naltrexone in combination with the POMC activator, relative to naltrexone alone (that is the extra effectiveness that naltrexone conferred to the POMC activator). Also listed are the mean effects of the drugs alone.

|  | Hour 1 | | Hour 2 | | Hour 4 | | Hour 8 | | Hour 8 | |
| --- | --- | --- | --- | --- | --- | --- | --- | --- | --- | --- |
|  | MEAN | SEM (±) | MEAN | SEM (±) | MEAN | SEM (±) | MEAN | SEM (±) | MEAN | SEM (±) |
| Saline | 1.00 | 0.0690 | 1.00 | 0.062 | 1.00 | 0.047 | 1.00 | 0.052 | 1.00 | 0.042 |
| AM 251 | 0.97 | 0.086 | 0.85 | 0.060 | 0.88 | 0.057 | 0.90 | 0.036 | 0.99 | 0.054 |
| Fluvoxamine | 0.77 | 0.058 | 0.85 | 0.056 | 0.95 | 0.044 | 0.91 | 0.034 | 0.92 | 0.054 |
| Nalmefene | 0.0083 | 0.0062 | 0.11 | 0.061 | 0.57 | 0.11 | 0.81 | 0.068 | 0.98 | 0.027 |
| AM 251 + Nalmefene | 0.010 | 0.010 | 0.075 | 0.055 | 0.30 | 0.1 | 0.62 | 0.042 | 0.90 | 0.021 |
| Fluvoxamine + Nalmefene | 0.0041 | 0.0041 | 0.019 | 0.012 | 0.42 | 0.087 | 0.79 | 0.026 | 0.99 | 0.031 |
| Bupropion | 0.32 | 0.044 | 0.64 | 0.049 | 0.97 | 0.048 | 0.96 | 0.036 | 0.99 | 0.020 |
| Naltrexone | 0.41 | 0.040 | 0.77 | 0.060 | 0.99 | 0.062 | 1.1 | 0.048 | 0.98 | 0.030 |
| Naltrexone + Bupropion | 0.042 | 0.0068 | 0.34 | 0.10 | 0.89 | 0.055 | 0.97 | 0.044 | 0.95 | 0.028 |
| Naltrexone | 0.30 | 0.10 | 0.56 | 0.050 | 0.83 | 0.10 | 0.98 | 0.19 | 1.01 | 0.22 |
| Fluoxetine | 0.36 | 0.030 | 0.57 | 0.13 | 0.68 | 0.15 | 0.76 | 0.21 | 1.05 | 0.22 |
| Naltrexone + Fluoxetine | 0.070 | 0.030 | 0.26 | 0.060 | 0.72 | 0.11 | 0.95 | 0.18 | 1.04 | 0.26 |

Example 9

Electrophysiology Data

To test the hypothesis that drugs selectively activate POMC neurons, we used a strain of transgenic mice expressing green fluorescent protein (EGFP, Clontech), under the transcriptional control of mouse Pomc genomic sequences that include a region located between −13 kb and −2 kb required for accurate neuronal expression Bright green fluorescence (509 nm) was seen in the two CNS regions where POMC is produced: the ARC and the nucleus of the solitary tract. Under ultraviolet (450-480 nm) excitation, POMC neurons were clearly distinguished from adjacent, non-fluorescent neurons visualized under infrared optics.

| Fenfluramine | 2X increase (n = 6) |
| --- | --- |
| Fenfluramine + Naltrexone | 5.2X (n = 8) |
| Fluoxetine | 3X (n = 1) |
| Fluoxetine + Naltrexone | 1.2X (n = 1) |
| Dopamine | 11X (n = 9) |
| Dopamine + Naltrexone | 1.5X (n = 3) |

Naltrexone alone has a potent (7x) but variable effect. many cells did not respond to naltrexone alone, but gave a significant response to combination treatment. Heisler et al. (Science 297(5581):609-11 (2002)) show that fenfluramine alone causes a 200% effect.

The results are set forth in the table below:

| Drug | Dose | Effect (%) | Drug | Dose | Effect (%) | Ratio |
|---|---|---|---|---|---|---|
| Naltrexone | 1 μM | 29650 | Naltrexone + Fenfluramine | 1 μM + 20 μM | 15080 | 0.51 |
| Naltrexone | 1 μM | 2200 | Naltrexone + Fenfluramine | 1 μM + 20 μM | 11440 | 520 |
| Naltrexone | 1 μM | 2500 | Naltrexone + Fenfluramine | 1 μM + 20 μM | 856 | 0.34 |
| Naltrexone | 1 μM | 417 | Naltrexone + Fenfluramine | 1 μM + 20 μM | 5700 | 13.67 |
| Naltrexone | 1 μM | 177 | Naltrexone + Fenfluramine | 1 μM + 20 μM | 430 | 2.43 |
| Naltrexone | 1 μM | 200 | Naltrexone + Fenfluramine | 1 μM + 20 μM | 2933 | 14.67 |
| Naltrexone | 1 μM | 700 | Naltrexone + Fenfluramine | 1 μM + 20 μM | | |
| Naltrexone | 1 μM | 900 | Naltrexone + Fenfluramine | 1 μM + 20 μM | 1831 | 2.03 |
| Naltrexone | 1 μM | 2273 | Naltrexone + Fenfluramine | 1 μM + 20 μM | | |
| Naltrexone | 1 μM | 300 | Naltrexone + Fenfluramine | 1 μM + 20 μM | 920 | 3.07 |

What is claimed is:

1. A composition for affecting weight loss comprising:
   (a) a sustained release formulation of bupropion or a pharmaceutically acceptable salt thereof in an amount effective to induce weight loss in an individual; and
   (b) a sustained release formulation of naltrexone or a pharmaceutically acceptable salt thereof in an amount effective to enhance the weight loss effect of the bupropion or salt thereof;
   wherein said composition is in a single oral dosage form fixed combination.

2. The composition of claim 1, wherein said composition comprises about 5 mg to about 50 mg of naltrexone or a pharmaceutically acceptable salt thereof.

3. The composition of claim 1, wherein said composition comprises about 30 mg to about 500 mg of bupropion or a pharmaceutically acceptable salt thereof.

4. The composition of claim 1, wherein said composition comprises about 5 mg to about 50 mg of naltrexone or a pharmaceutically acceptable salt thereof, and about 30 mg to about 500 mg of bupropion or a pharmaceutically acceptable salt thereof.

5. A pharmaceutical composition for affecting weight loss comprising:
   (a) a sustained release formulation of bupropion or a pharmaceutically acceptable salt thereof in an amount effective to induce weight loss in an individual;
   (b) a sustained release formulation of naltrexone or a pharmaceutically acceptable salt thereof in an amount effective to enhance the weight-reducing effect of the bupropion or salt thereof; and
   a pharmaceutically acceptable excipient, diluent, or carrier, wherein said composition is formulated into a single oral fixed combination dosage form.

6. The pharmaceutical composition of claim 5, wherein said composition comprises about 5 mg to about 50 mg of naltrexone or a pharmaceutically acceptable salt thereof.

7. The pharmaceutical composition of claim 5, wherein said composition comprises about 30 mg to about 500 mg of bupropion or a pharmaceutically acceptable salt thereof.

8. The pharmaceutical composition of claim 5, wherein said composition comprises about 5 mg to about 50 mg of naltrexone or a pharmaceutically acceptable salt thereof, and about 30 mg to about 500 mg of bupropion or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 7,375,111 B2 | Page 1 of 1 |
| APPLICATION NO. | : 10/828795 | |
| DATED | : May 20, 2008 | |
| INVENTOR(S) | : Eckard Weber and Michael Alexander Cowley | |

It is certified that error appears in the above-identified patent and that said Letters Patent is hereby corrected as shown below:

Page 2, column 2, line 31, delete "1730:" and insert -- 1730; --

Page 2, column 2, line 72, after "reducing" insert -- effects --

Page 3, column 1, line 4, delete "Brian" and insert -- Brain --

Page 3, column 2, line 1, delete "Enchancement" and insert -- Enhancement --

Page 4, column 2, line 21, after "Caffeine" insert -- and --

Column 2, line 63, delete "1-opioid" and insert -- μ-opioid --

Column 3, line 40, delete "A-MSH," and insert -- α-MSH, --

Column 5, line 57, delete "fosphenyloin" and insert -- fosphenytoin --

Column 5, line 57, delete "phenyloin" and insert -- phenytoin --

Column 9, line 49, delete "1-Subtype" and insert -- μ-Subtype --

Column 30, line 67, delete "η-opioid" and insert -- κ-opioid --

Column 41, lines 34-35, in Claim 1, delete "oral dosage form fixed combination." and insert -- oral fixed combination dosage form. --

Signed and Sealed this

Eleventh Day of November, 2008

JON W. DUDAS
*Director of the United States Patent and Trademark Office*